United States Patent
Baba

(10) Patent No.: US 11,402,907 B2
(45) Date of Patent: Aug. 2, 2022

(54) INFORMATION PROCESSING SYSTEM AND NON-TRANSITORY COMPUTER READABLE MEDIUM

(71) Applicant: Agama-X Co., Ltd, Tokyo (JP)

(72) Inventor: Motofumi Baba, Tokyo (JP)

(73) Assignee: Agama-X Co., Ltd., Tokyo (JP)

( * ) Notice: Subject to any disclaimer, the term of this patent is extended or adjusted under 35 U.S.C. 154(b) by 0 days.

(21) Appl. No.: 16/891,596

(22) Filed: Jun. 3, 2020

(65) Prior Publication Data

US 2021/0165489 A1 Jun. 3, 2021

(30) Foreign Application Priority Data

Dec. 3, 2019 (JP) .............................. JP2019-219153

(51) Int. Cl.
*G06F 3/01* (2006.01)
*G10L 15/22* (2006.01)
*G06V 40/16* (2022.01)

(52) U.S. Cl.
CPC ............ *G06F 3/015* (2013.01); *G06V 40/174* (2022.01); *G10L 15/22* (2013.01); *G10L 2015/223* (2013.01)

(58) Field of Classification Search
CPC .......... G06F 3/015; G06F 3/012; G06F 3/013; G06F 3/005; G06K 9/00302; G10L 15/22; G10L 2015/223
See application file for complete search history.

(56) References Cited

U.S. PATENT DOCUMENTS

| 2013/0096453 | A1  | 4/2013  | Chung et al. |
| 2014/0108309 | A1* | 4/2014  | Frank ..................... G07C 13/00 706/12 |
| 2017/0042439 | A1* | 2/2017  | Yeow ..................... A61B 5/165 |
| 2018/0333575 | A1* | 11/2018 | Bouton ................ A61B 5/4836 |
| 2019/0247662 | A1* | 8/2019  | Poltroak ............... A61B 5/246 |

OTHER PUBLICATIONS

Ratti et al., Comparison of Medical and Consumer Wireless EEG Systems for Use in Clinical Trials, Frontiers in Human Neuroscience, Aug. 3, 2017, vol. 11, Article 398, pp. 1-7.

* cited by examiner

*Primary Examiner* — Robert J Michaud
(74) *Attorney, Agent, or Firm* — Hoffman Warnick LLC

(57) ABSTRACT

An information processing system includes a processor configured to determine an operation based on a combination of first features of first biological information detected from a user and second features of second, different biological information detected from the user, the user being monitored for both the first biological information and the second biological information simultaneously, the first biological information being brain waves, and instruct a device to perform the operation.

24 Claims, 34 Drawing Sheets

| No. | FEATURES OF BRAIN WAVE INFORMATION | OPERATION (OPERATION SIGNAL) |
|---|---|---|
| ... | | |
| 10010 | FEATURES AA | TURN ON |
| 10011 | FEATURES AB | TURN OFF |
| ... | | |

| No. | FEATURES OF BIOLOGICAL INFORMATION OTHER THAN BRAIN WAVES | OPERATION (OPERATION SIGNAL) |
|---|---|---|
| ... | | |
| 20010 | FEATURES #102 | TURN ON |
| 20011 | FEATURES #103 | TURN OFF |
| ... | | |

| TIME | FEATURES OF BRAIN WAVE INFORMATION | ESTIMATED OPERATION (OPERATION SIGNAL) | OPERATION INDICATED BY SOUND | CORRECT/ INCORRECT |
|---|---|---|---|---|
| ... | | | | |
| 10/15/20XX 12:45:52 | FEATURES AA | TURN ON | TURN ON | CORRECT |
| 10/15/20XX 12:46:10 | FEATURES BB | STOP | PLAYBACK | INCORRECT |
| ... | | | | |

| TIME | FEATURES OF BIOLOGICAL INFORMATION OTHER THAN BRAIN WAVES | ESTIMATED OPERATION (OPERATION SIGNAL) | OPERATION INDICATED BY SOUND | CORRECT/ INCORRECT |
|---|---|---|---|---|
| ... | | | | |
| 10/15/20XX 12:45:52 | FEATURES #102 | TURN ON | TURN ON | CORRECT |
| 10/15/20XX 12:46:10 | FEATURES #111 | PLAYBACK | PLAYBACK | CORRECT |
| ... | | | | |

FIG. 27

| TIME | TYPE OF OPERATION INDICATED BY SOUND | FEATURES OF BRAIN WAVE INFORMATION | FEATURES OF BIOLOGICAL INFORMATION OTHER THAN BRAIN WAVES | OPERATION ESTIMATED FROM FEATURES OF BRAIN WAVE INFORMATION | CORRECT/ INCORRECT | OPERATION ESTIMATED FROM BIOLOGICAL INFORMATION OTHER THAN BRAIN WAVES | CORRECT/ INCORRECT | OPERATION INDICATED BY OPERATION SIGNAL |
|---|---|---|---|---|---|---|---|---|
| ... | | | | | | | | |
| 10/15/20XX 12:45:52 | TURN ON | FEATURES AA | FEATURES #102 | TURN ON | CORRECT | TURN ON | CORRECT | TURN ON |
| 10/15/20XX 12:46:10 | PLAYBACK | FEATURES BB | FEATURES #111 | STOP | INCORRECT | PLAYBACK | CORRECT | PLAYBACK |
| ... | | | | | | | | |

235

INFORMATION PROCESSING SYSTEM AND NON-TRANSITORY COMPUTER READABLE MEDIUM

CROSS-REFERENCE TO RELATED APPLICATIONS

This application is based on and claims priority under 35 USC 119 from Japanese Patent Application No. 2019-219153 filed Dec. 3, 2019.

BACKGROUND

(i) Technical Field

The present disclosure relates to an information processing system and a non-transitory computer readable medium.

(ii) Related Art

It is desired to use brain waves as a user interface of a next generation (e.g., refer to U.S. Patent Application Publication No. 2013/0096453).

SUMMARY

In order to use brain waves as a user interface, a user needs to be able to generate certain types of brain waves intentionally, but it requires special training to achieve this with a certain level of reproducibility. Although measurement of brain waves at positions other than measurement points specified in a medical field has been studied, the accuracy of association with a user's intention is low. It is therefore expected that, at an initial stage of development of such a user interface, a mechanism for improving the accuracy of operation by complementing measured brain waves will be required.

Aspects of non-limiting embodiments of the present disclosure relate to improve the accuracy of operation of a device compared to when only brain waves are used.

Aspects of certain non-limiting embodiments of the present disclosure overcome the above disadvantages and/or other disadvantages not described above. However, aspects of the non-limiting embodiments are not required to overcome the disadvantages described above, and aspects of the non-limiting embodiments of the present disclosure may not overcome any of the disadvantages described above.

According to an aspect of the present disclosure, there is provided an information processing system including a processor configured to determine an operation based on a combination of first features of first biological information detected from a user and second features of second, different biological information detected from the user, the user being monitored for both the first biological information and the second biological information simultaneously, the first biological information being brain waves, and instruct a device to perform the operation.

BRIEF DESCRIPTION OF THE DRAWINGS

Exemplary embodiments of the present disclosure will be described in detail based on the following figures, wherein:

FIGS. 6A and 6B are diagrams illustrating an example of correspondence tables used in the first exemplary embodiment: FIG. 6A illustrates a correspondence table for features of brain wave information and FIG. 6B illustrates a correspondence table for features of biological information other than brain waves;

FIG. 12A illustrates a result of measurement at a time when an open eye state and a closed eye state are alternated twice without blinking and FIG. 12B illustrates a result of measurement at a time when the open eye state and the closed eye state are alternated twice with blinking;

FIG. 13A illustrates a result of measurement at a time when the open eye state and the closed eye state are alternated twice without blinking and FIG. 13B illustrates a result of measurement at a time when the open eye state and the closed eye state are alternated with blinking and movement of the jaw;

FIG. 14A illustrates changes in the percentage of spectral intensity in each frequency band at a time when subjects have entered the closed eye state from the open eye state with blinking, FIG. 14B illustrates changes in the percentage of spectral intensity in each frequency band at a time when the subjects have entered the closed eye state from the open eye state without blinking, and FIG. 14C illustrates a case where α waves do not increase;

FIG. 15A illustrates changes in the percentage of spectral intensity in each frequency band at a time when the subjects have entered the closed eye state from the open eye state with blinking, FIG. 15B illustrates changes in the percentage of spectral intensity in each frequency band at a time when the subjects have entered the closed eye state from the open eye state without blinking, and FIG. 15C illustrates a case where α waves do not increase;

FIG. 16A illustrates a result of the measurement performed with MindWave and FIG. 16B illustrates a result of the measurement performed with the earphones used in the first exemplary embodiment;

FIGS. 23A and 23B are diagrams illustrating an example of tables storing a history of operations and information indicating whether the operations are correct: FIG. 23A illustrates a table storing a history of operations estimated from features of brain wave information and information indicating whether operations are correct and FIG. 23B illustrates a table storing a history of operations estimated from features of biological information other than brain waves and information indicating whether the operations are correct;

FIG. 27 is a diagram illustrating an example of a table storing a history of operations based on brain waves and information indicating whether the operations are correct;

FIG. 33A illustrates a case where the user's line of sight is leftward, FIG. 33B illustrates a case where the user's line of sight is rightward, FIG. 33C illustrates a case where the user's line of sight is upward, and FIG. 33D illustrates a case where the user's line of sight is downward;

DETAILED DESCRIPTION

Exemplary embodiments of the present disclosure will be described hereinafter with reference to the drawings.

First Exemplary Embodiment

System Configuration

Figure 1:
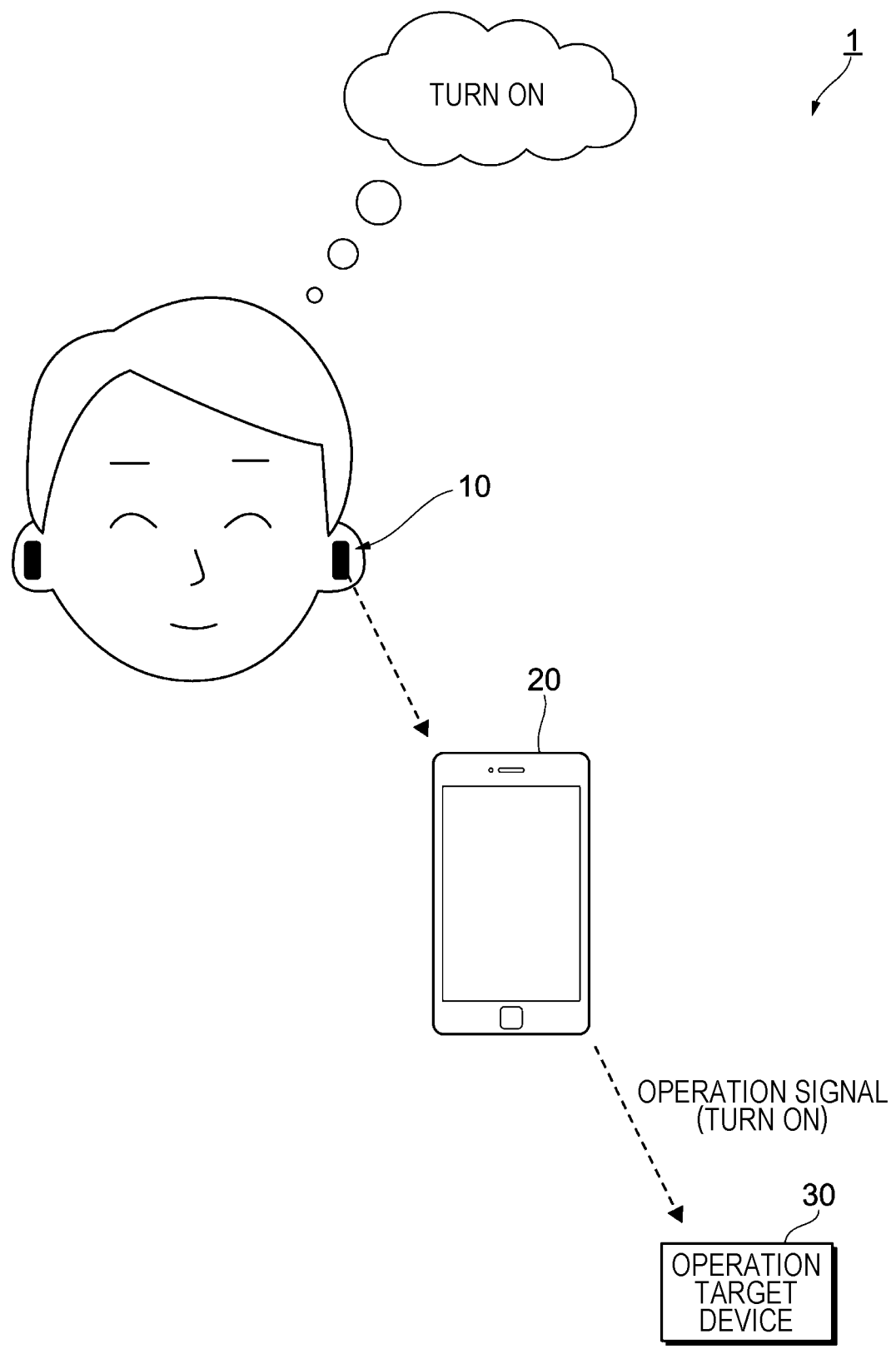
FIG. 1 is a diagram illustrating a schematic configuration of a brain wave operation system used in a first exemplary embodiment.

FIG. 1 is a diagram illustrating a schematic configuration of a brain wave operation system 1 used in a first exemplary embodiment.

The brain wave operation system 1 illustrated in FIG. 1 includes earphones 10 inserted into the external auditory meatuses, an information terminal 20 wirelessly connected to the earphones 10, and a device (hereinafter referred to as an "operation target device") 30 to be operated by a user.

The earphones 10 and the information terminal 20 according to the present exemplary embodiment constitute an example of an information processing system.

The earphones 10 according to the present exemplary embodiment include a circuit that plays back sound received from the information terminal 20 and a circuit that measures electrical signals (hereinafter referred to as "brain waves") caused by brain activity.

The earphones 10 used in the present exemplary embodiment are a wireless device. The earphones 10, therefore, are connected to the information terminal 20 through wireless communication.

In the present exemplary embodiment, Bluetooth (registered trademark) is used for the wireless connection between the earphones 10 and the information terminal 20. Alternatively, another communication standard such as Wi-Fi (registered trademark) may be used for the wireless connection, although the earphones 10 and the information terminal 20 may be connected to each other by cable.

The information terminal 20 estimates an operation desired by the user by processing a digital signal received from the earphones 10 and transmits a signal (hereinafter referred to as an "operation signal") indicating the estimated operation to the operation target device 30. In the example illustrated in FIG. 1, a smartphone is used as the information terminal 20. Alternatively, the information terminal 20 may be a tablet terminal, a laptop computer, a wearable computer, or the like.

In FIG. 1, an operation signal corresponding to "turn on" desired by the user in his/her mind is transmitted to the operation target device 30. Infrared radiation or another existing communication scheme such as a low-power wide-area (LPWA) network may be used for the transmission of the operation signal to the operation target device 30. The LPWA network is an example of a communication scheme used for Internet of Things (IoT) communication.

The operation target device 30 according to the present exemplary embodiment may be any device having a function of receiving signals from the outside and controlling operations inside thereof. The operation target device 30 is, for example, a device including an infrared reception unit or a device that achieves IoT communication.

In FIG. 1, the operation target device 30 receives the operation signal corresponding to "turn on" desired by the user in his/her mind from the information terminal 20.

First, a reason why the earphones 10 are used to measure brain waves will be described.

When interfaces employing brain waves will begin to spread in the future, users might not like wearing devices visibly designed to measure brain waves. Helmet-shaped devices, for example, might not gain popularity in terms of both design and a burden on the body.

For this reason, the earphones 10 are used in the present exemplary embodiment as a device for measuring brain waves. Since the earphones 10 are already widely used as an audio device, users will not be reluctant to wear the earphones 10.

In addition, since the external auditory meatuses, into which the earphones 10 are inserted, are close to the brain, brain waves can be easily measured. How the earphones 10 can measure brain waves will be described later in a "Results of Experiments" section. The external auditory meatuses are examples of the ears. In the present exemplary embodiment, the ears include the auricles and the external auditory meatuses.

In addition, because the earphones 10 each include a speaker, which is not illustrated, information can be easily transmitted to the user.

In addition, because the ears into which the earphones 10 are inserted are close to the user's mouth, voices uttered by the user can be easily detected.

Configuration of Earphones 10

Figure 2:
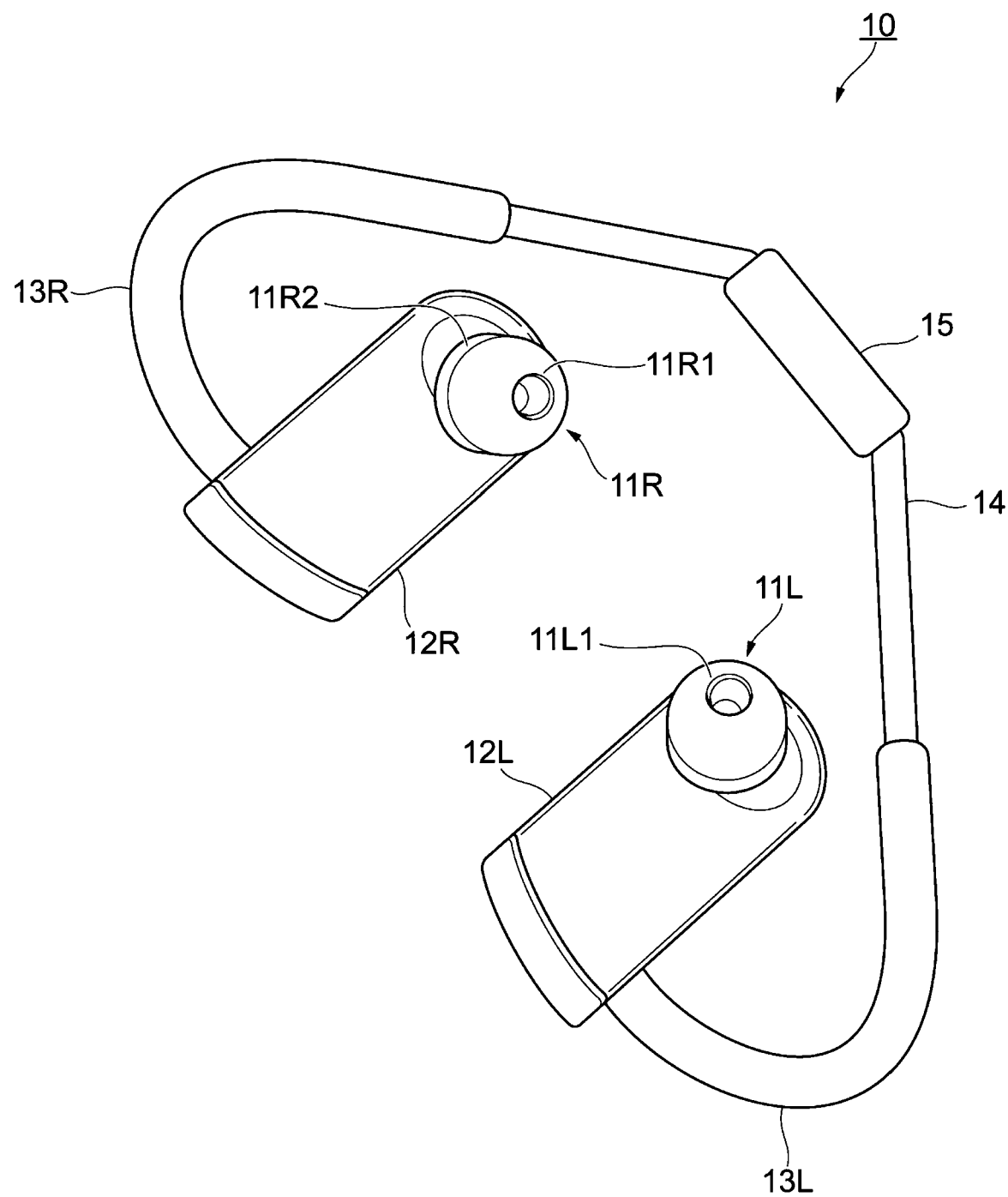
FIG. 2 is a diagram illustrating an example of the appearance of earphones used in the first exemplary embodiment.

FIG. 2 is a diagram illustrating an example of the appearance of the earphones 10 used in the first exemplary embodiment.

The earphones 10 include earphone chips 11R and 11L inserted into the external auditory meatuses, earphone bodies 12R and 12L on which the earphone chips 11R and 11L are mounted, respectively, ear hooks 13R and 13L attached between the auricles and the temples, a cable 14 connecting the earphone bodies 12R and 12L to each other, and a controller 15 on which a power button and volume buttons are provided.

"R" in FIG. 2 denotes that a corresponding part is located on a side of the user's right ear, and "L" denotes a corresponding part is located on a side of the user's left ear.

The earphone chip 11R according to the present exemplary embodiment is inserted in the external auditory meatus and includes a dome-shaped electrode 11R1 that comes into contact with an inner wall of the external auditory meatus and a ring-shaped electrode 11R2 that comes into contact with the concha cavity.

The electrodes 11R1 and 11R2 according to the present exemplary embodiment are composed of conductive rubber in order to measure electrical signals observed on the skin. The electrodes 11R1 and 11R2 are electrically insulated from each other by an insulator.

In the present exemplary embodiment, the electrode 11R1 is a terminal used to measure potential variations including brain waves (electroencephalogram (EEG)) and biological information other than the brain waves (hereinafter referred to as an "EEG measuring terminal"). In the present exemplary embodiment, the biological information other than brain waves is components of electrical signals caused by movement of muscles relating to facial expression, such as ones relating to the eyes, nose, mouth, and eyebrows (hereinafter referred to as "mimic muscles"), muscles for masticatory movement (hereinafter referred to as "masseter muscles"), and muscles for swallowing (hereinafter referred to as "hyoid muscles"), and the like.

The electrode 11R2 is a ground electrode (hereinafter referred to as a "GND terminal").

The earphone chip 11L, on the other hand, includes a dome-shaped electrode 11L1 that is inserted into the external auditory meatus and that comes into contact with an inner wall of the external auditory meatus. In the present exemplary embodiment, the electrode 11L1 is a terminal used to measure a reference (REF) potential (hereinafter referred to as a "REF terminal"). In the present exemplary embodiment, the electrode 11R2 and the electrode 11L1 are electrically short-circuited to each other.

As described later, in the present exemplary embodiment, potential variations including brain waves and biological information other than brain waves are measured as differential signals between electrical signals measured by the electrodes 11R1 and 11L1.

Potential variations including brain waves and biological information other than brain waves will be generically referred to as "biological information such as brain waves" hereinafter.

In the field of brain science, all potential variations derived from biological information other than brain waves are called "artifacts". It is considered that electrical signals obtained by measuring brain waves invariably include artifacts.

Components included in artifacts are classified into those derived from a living body, those derived from a measurement system such as electrodes, and those derived from external devices and environment. Among these three types of component, the components other than those derived from a living body can be measured as noise detected by the earphones 10. The noise can be measured as electrical signals at a time when the electrodes 11R1 and 11L1 are electrically short-circuited to each other.

The earphone body 12R according to the present exemplary embodiment includes a circuit that generates digital signals corresponding to biological signals such as brain waves, a circuit that generates audio data from electrical signals output from a microphone, which is not illustrated, and a circuit that performs a process for decoding audio data received from the information terminal (refer to FIG. 1) and outputting the decoded audio data to the speaker, which is not illustrated.

The earphone body 12L, on the other hand, includes a battery.

Figure 3:
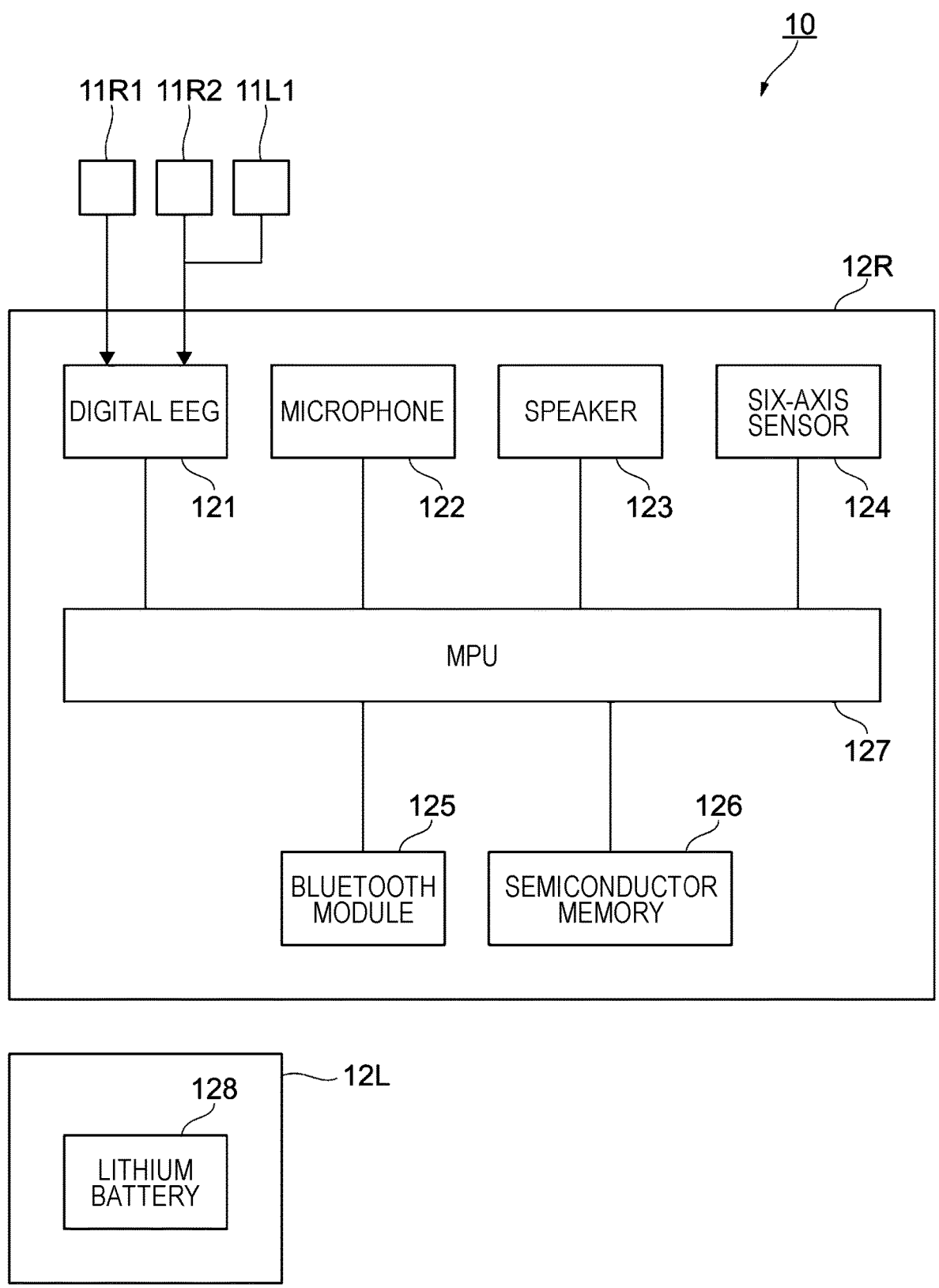
FIG. 3 is a diagram illustrating an example of the internal configuration of the earphones used in the first exemplary embodiment.

FIG. 3 is a diagram illustrating an example of the internal configuration of the earphones 10 used in the first exemplary embodiment.

FIG. 3 illustrates the internal configuration of the earphone bodies 12R and 12L of the earphones 10.

In the present exemplary embodiment, the earphone body 12R includes a digital electroencephalograph (EEG) 121, a microphone 122, a speaker 123, a six-axis sensor 124, a Bluetooth module 125, a semiconductor memory 126, and a microprocessor unit (MPU) 127.

The digital EEG 121 includes a differential amplifier that differentially amplifies potential variations detected by the electrodes 11R1 and 11L1, a sampling circuit that samples an output of the differential amplifier, and an analog-to-digital (A/D) conversion circuit that converts an analog potential after the sampling into a digital value. In the present exemplary embodiment, a sampling rate is 600 Hz. The resolution of the A/D conversion circuit is 16 bits.

The microphone 122 includes a diaphragm that vibrates in accordance with sounds uttered by the user, a voice coil that converts the vibration of the diaphragm into electrical signals, and an amplifier that amplifies the electrical signals. An A/D conversion circuit that converts the analog potential of the electrical signals output from the amplifier into digital values is separately prepared.

The speaker 123 includes a diaphragm and a voice coil that vibrates the diaphragm using a current according to audio data. Audio data input from the MPU 127 is converted by a digital-to-analog (D/A) conversion circuit into an analog signal.

The six-axis sensor 124 includes a three-axis acceleration sensor and a three-axis gyro sensor. The six-axis sensor 124 detects an attitude of the user.

The Bluetooth module 125 communicates data with the information terminal 20 (refer to FIG. 1). In the present exemplary embodiment, the Bluetooth module 125 transmits digital signals output from the digital EEG 121 and audio data obtained by the microphone 122 and receives audio data from the information terminal 20.

The semiconductor memory 126 includes, for example, a read-only memory (ROM) storing basic input-output system (BIOS), a random-access memory (RAM) used as a working area, and a rewritable nonvolatile memory (hereinafter referred to as a "flash memory").

In the present exemplary embodiment, the flash memory stores digital signals, which are outputs of the digital EEG 121, audio data obtained by the microphone 122, audio data received from the information terminal 20, and the like.

The MPU 127 controls communication of digital signals with the information terminal 20, processes digital signal to be transmitted to the information terminal 20, and processes digital signals received from the information terminal 20. In the present exemplary embodiment, the MPU 127 performs a process, such as a Fourier transform, on digital signals output from the digital EEG 121. The MPU 127 and the semiconductor memory 126 operate as a computer.

The earphone body 12L, on the other hand, includes a lithium battery 128.

Configuration of Information Terminal 20

Figure 4:
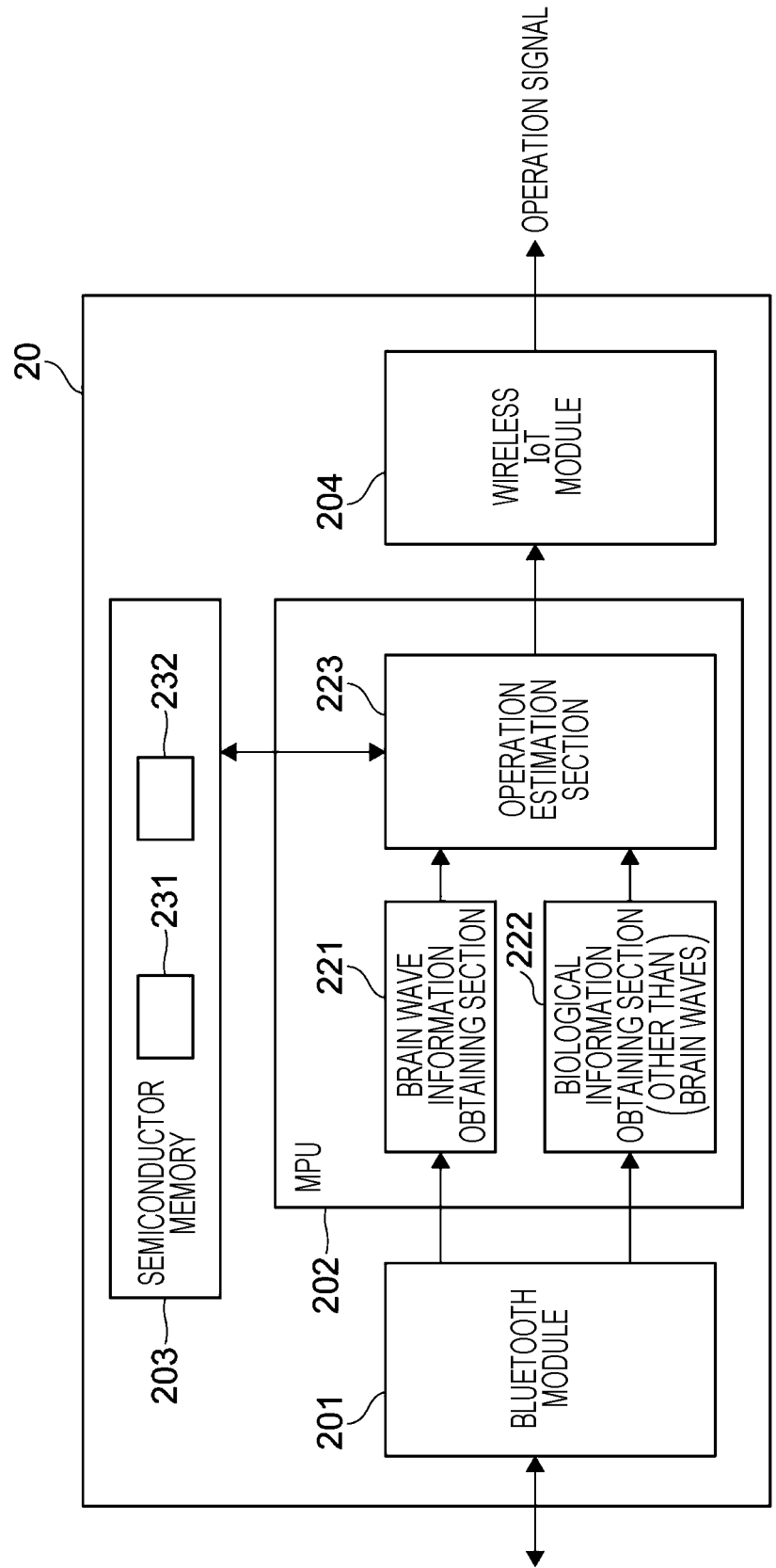
FIG. 4 is a diagram illustrating an example of the internal configuration of an information terminal used in the first exemplary embodiment.

FIG. 4 is a diagram illustrating an example of the internal configuration of the information terminal 20 used in the first exemplary embodiment.

FIG. 4 illustrates only devices of the information terminal 20 relating to generation of an operation signal for operating the operation target device 30 (refer to FIG. 1) on the basis of biological information such as brain waves.

The information terminal 20 illustrated in FIG. 4 includes a Bluetooth module 201, an MPU 202, a semiconductor memory 203, and a wireless IoT module 204.

The Bluetooth module 201 is used to communicate with the Bluetooth module 125 provided for the earphones 10.

The MPU 202 executes a function of obtaining, from a digital signal received from the earphones 10 (refer to FIG. 1), information regarding brain waves (hereinafter referred to as "brain wave information") and biological information other than the brain waves and estimating an operation to be performed on the operation target device 30 (refer to FIG. 1). The function is achieved by executing an application program.

The MPU 202 illustrated in FIG. 4 functions as a brain wave information obtaining section 221 that obtains features of brain wave information from a digital signal received from the earphones 10, a biological information obtaining section 222 that obtains features of biological information other than brain waves from a digital signal received from the earphones 10, and an operation estimation section 223 that estimates an operation to be performed on the operation target device 30 in accordance with a combination of features of brain wave information and features of biological information other than brain waves.

The brain wave information obtaining section 221 separates a waveform component unique to brain waves observed in a digital signal received from the earphones 10 and obtains features of brain wave information included in the separated wave form component. An independent component analysis (ICA) or another known technique is used to obtain features of brain wave information. The features of brain wave information include, for example, a waveform component unique to brain waves observed in a digital signal, the spectral intensity and distribution of each frequency component included in the waveform component, the spectral intensity of a certain frequency component included in the waveform component, and the percentage of increase in α waves.

The biological information obtaining section 222 obtains, as features of biological information other than brain waves, potential variations caused by an intentional movement of head muscles by the user while the user is desiring a certain operation in his/her mind. The features of biological information other than brain waves include, for example, a waveform component unique to biological information other than brain waves observed in a digital signal, the spectral intensity and distribution of each frequency component included in the waveform component, and the spectral intensity of a certain frequency component included in the waveform component.

A reason why potential variations caused by an intentional movement of head muscles by the user while the user is desiring a certain operation in his/her mind is as follows.

As described above, biological information other than brain waves invariably mix with an electrical signal caused by brain waves. Biological information other than brain waves, therefore, has been considered as information that prevents measurement of brain wave information.

In addition, although it is easy to desire a certain operation in one's mind, it is not necessarily easy to intentionally generate brain waves corresponding to a certain operation. It is needless to say that some practice is required to output such brain waves with a high level of reproducibility. Furthermore, it has been pointed out that it is difficult for different users to reproduce similar brain waves.

It is much easier, however, for a user to intentionally move certain muscles than to output certain brain waves. That is, it is not difficult for a user to cause certain features of biological information.

In the present exemplary embodiment, therefore, an electrical signal caused by movement of head muscles, which can be intentionally moved by the user, is obtained as features of biological information, and features of brain wave information are complemented by the obtained features.

Figure 5:
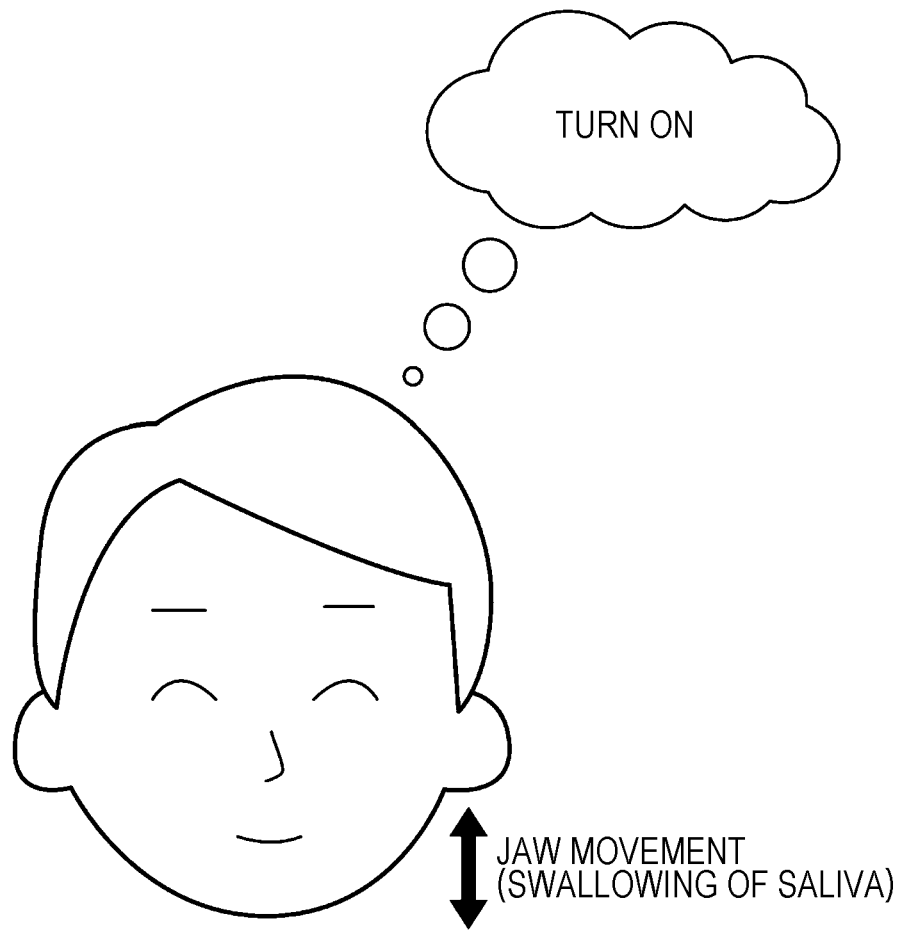
FIG. 5 is a diagram illustrating an example of an intentional movement of muscles by a user while the user is desiring a certain operation in his/her mind.

FIG. 5 is a diagram illustrating an example of the intentional movement of muscles by the user while the user is desiring a certain operation in his/her mind. FIG. 5 illustrates an example of movement of the jaw accompanied by swallowing of saliva. As described above, although it needs some practice and experience to output certain brain waves, most users can intentionally swallow saliva. In addition, as described later, an electrical signal caused by movement of muscles has a larger amplitude than a waveform of brain waves and can be easily distinguished from brain wave information. Furthermore, an electrical signal caused by movement of muscles is intermittent and does not prevent measurement of brain wave information while the muscles are not moving.

For this reason, features of biological information other than brain waves can be obtained while obtaining features of brain wave information, which are observed while the user is desiring a certain operation in his/her mind.

FIG. 4 will be referred to again.

The operation estimation section 223 according to the present exemplary embodiment estimates an operation corresponding to each set of features by referring to correspondence tables prepared for features of brain wave information and features of biological information other than brain waves. The operation estimation section 223 then outputs the estimated operation on the basis of predetermined rules to the wireless IoT module 204 as an operation signal.

There are some methods for identifying an operation on the basis of the predetermined rules.

In one method, for example, if an operation can be estimated from features of brain wave information, the estimated operation takes priority over an operation estimated from features of biological information other than brain waves.

There is another method in which the user is asked whether an operation estimated from features of brain wave information is correct before an operation signal is output to the operation target device 30 (refer to FIG. 1).

The semiconductor 203 according to the present exemplary embodiment stores correspondence tables 231 and 232 used by the operation estimation section 223 to determine an operation.

FIGS. 6A and 6B are diagrams illustrating an example of the correspondence tables 231 and 232 used in the first exemplary embodiment. FIG. 6A illustrates the correspondence table 231 for features of brain wave information, and FIG. 6B illustrates the correspondence table 232 for features of biological information other than brain waves.

The correspondence table 231 includes management numbers, features of brain wave information, and corresponding operations.

In FIG. 6A, "turn on" is associated with features AA, and "turn off" is associated with features AB. The operations also include information for identifying an operation target device 30.

The correspondence table 232 includes management numbers, features of biological information other than brain waves, and corresponding operations.

In FIG. 6B, "turn on" is associated with features #102, and "turn off" is associated with features #103. For example, features observed when the user swallows saliva once are associated with "turn on", and features observed when the user swallows saliva twice are associated with "turn off". The operations also include information for identifying an operation target device 30.

Although correspondences stored in the correspondence table 232 are determined in advance in the present exemplary embodiment, the user may register new correspondences.

The semiconductor 203 also includes a ROM storing BIOS, a RAM used as a working area, and a flash memory, as well as the correspondence tables 231 and 232.

FIG. 4 will be referred to again.

In the present exemplary embodiment, the wireless IoT module 204 transmits an operation signal on the basis of a communication standard such as LPWA.

Processes Performed by Information Terminal 20

An example of processes performed by the information terminal 20 (refer to FIG. 1) by executing programs using the MPU 202 (refer to FIG. 4) will be described hereinafter.

First Process

In the first process, the user is not asked whether an operation is correct before the operation is performed on the basis of features of brain wave information.

Figure 7:
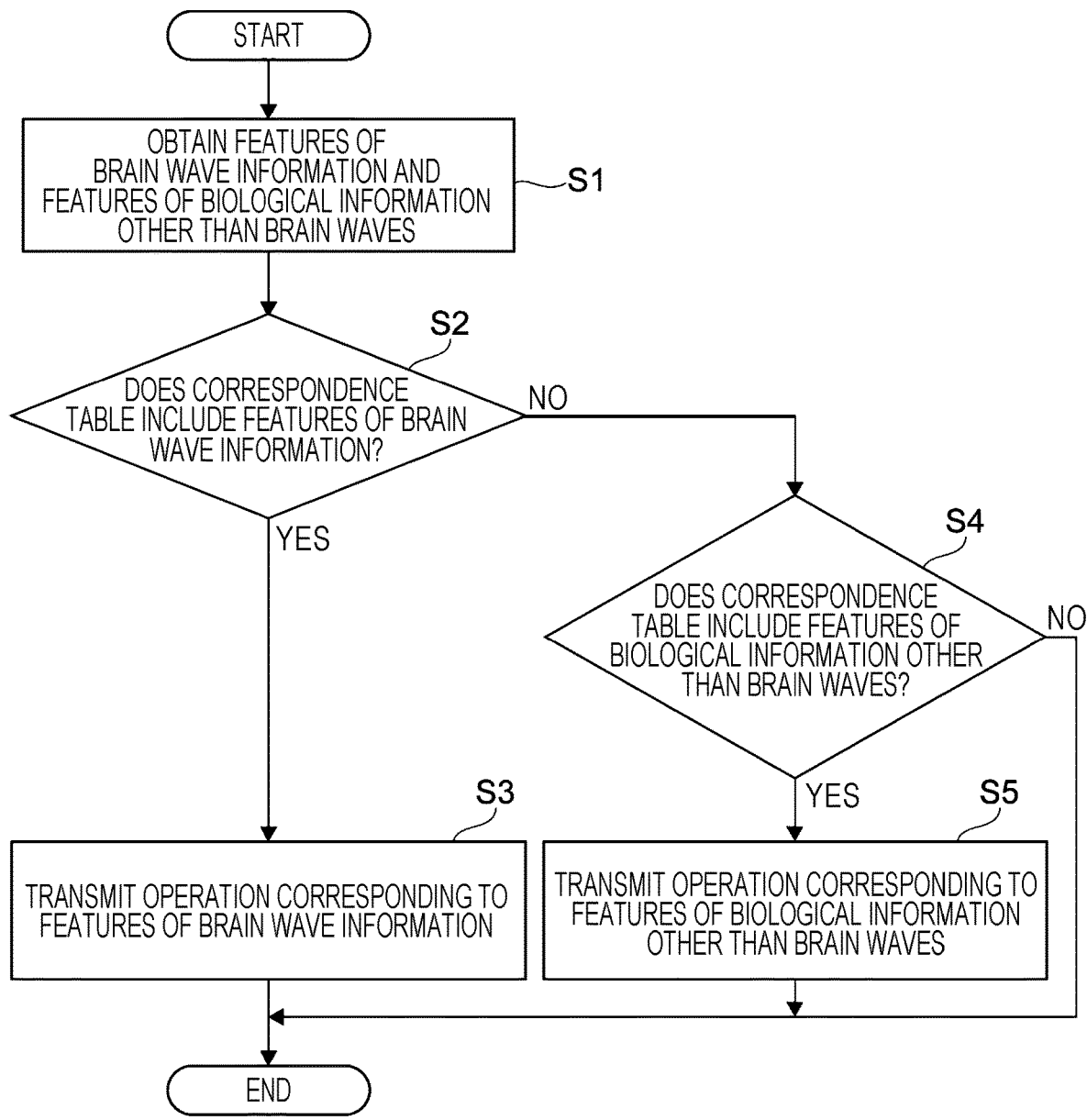
FIG. 7 is a flowchart illustrating an example of a process performed by the information terminal after the information terminal receives a digital signal including brain wave information.

FIG. 7 is a flowchart illustrating an example of a process performed by the information terminal 20 after the information terminal 20 receives a digital signal including brain wave information. "S" in FIG. 7 denotes a step.

In the present exemplary embodiment, digital information including brain wave information is transmitted to the information terminal 20 from the earphones 10 (refer to FIG. 1). The user moves his/her jaw in a certain way corresponding to a certain operation to be performed on the operation target device 30 (refer to FIG. 1) while desiring the operation in his/her mind.

Upon receiving the digital signal including the brain wave information from the earphones 10 (refer to FIG. 1), the MPU 202 obtains features of the brain wave information and features of biological information other than brain waves from the received digital signal (S1).

Next, the MPU 202 determines whether the correspondence table 231 (refer to FIG. 6A) includes the features of the brain wave information (S2).

If a result of S2 is positive, the MPU 202 transmits an operation corresponding to the features of the brain wave information (S3).

If the result of S2 is negative, on the other hand, the MPU 202 determines whether the correspondence table 232 (refer to FIG. 6B) includes the features of the biological information other than brain waves.

If a result of S4 is positive, the MPU 202 transmits an operation corresponding to the features of the biological information (S5).

If the result of S4 is negative, on the other hand, the MPU 202 ends the process. In this case, the user notices that the operation target device 30 is not performing any operation and his/her operation has failed.

Alternatively, if the result of S4 is negative, the user may be notified that no operation has been identified. For example, a message may be displayed on a display screen of the information terminal 20 (refer to FIG. 1) or output from the speaker 123 (refer to FIG. 3) provided for the earphones 10.

In the first process, the user can operate operation target device 30 on the basis of features caused by movement of muscles in his/her jaw, which can be intentionally moved by the user, before the user gets accustomed to performing operations through brain waves.

After getting accustomed to performing operations through brain waves and becoming able to intentionally reproduce certain brain waves, the user can operate the operation target device 30 without intentionally moving the muscles in his/her jaw or the like.

With the brain wave operation system 1 according to the present exemplary embodiment, operations based on brain waves can be performed while making the user feel less reluctant to wear a device for operating the operation target device 30 through brain waves. In addition, before the user gets accustomed to performing operations through brain waves, the user can complement operations based on brain waves by intentionally moving the muscles in his/her jaw or the like. After getting accustomed to performing operations through brain waves, the user can operate the operation target device 30 as intended by desiring certain operations in his/her mind without intentionally moving the muscles in his/her jaw or the like.

Second Process

It is assumed in the first process that, if features of brain wave information obtained by the brain wave information obtaining section 221 (refer to FIG. 4) are found in the correspondence table 231 (refer to FIG. 6), the found features and an operation desired in the user's mind match.

In the case of a user who is not accustomed to performing operations through brain waves, however, an operation desired in the user's mind and features of obtained brain waves might not match. The operation target device 30, therefore, can perform an unintended operation.

In a second process, therefore, a step of making the user check an operation estimated from features of brain wave information is added before the operation is transmitted to the operation target device 30.

Figure 8:
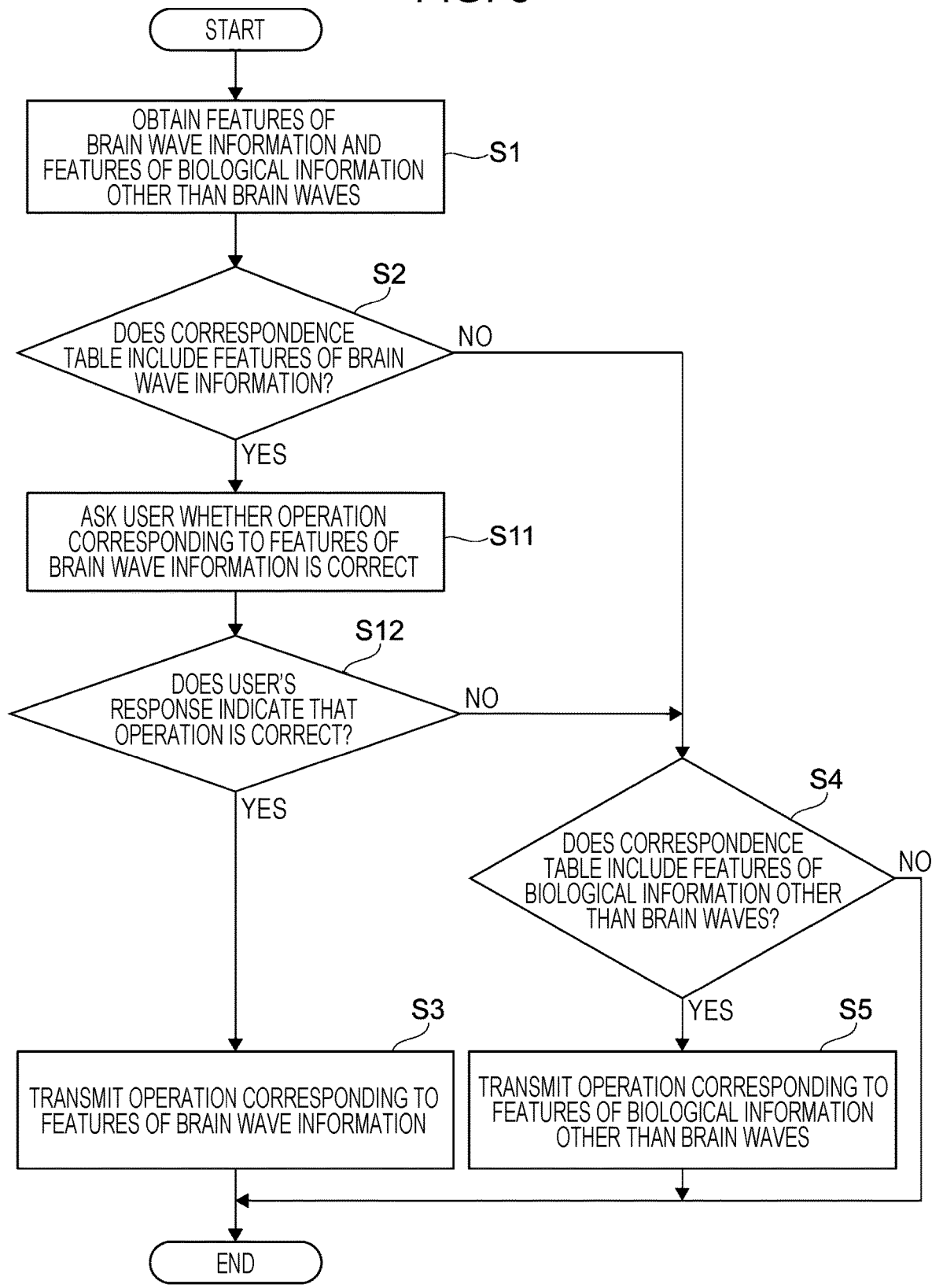
FIG. 8 is a flowchart illustrating another example of the process performed by the information terminal after the information terminal receives a digital signal including brain wave information.

FIG. 8 is a flowchart illustrating another example of the process performed by the information terminal 20 (refer to FIG. 1) after the information terminal 20 receives a digital signal including brain wave information. In FIG. 8, the same steps as in FIG. 7 are given the same reference numerals.

In this process, too, the MPU 202 that has received a digital signal including brain wave information from the earphones 10 obtains features of the brain wave information and features of biological information other than brain waves from the received digital signal (S1).

Next, the MPU 202 determines whether the correspondence table 231 includes the features of the brain wave information (S2).

If the result of S2 is positive, the MPU 202 asks the user whether an operation corresponding to the features of the brain wave information is correct (S11). Here, a message may be displayed on the display screen, which is not illustrated, of the information terminal 20 or output from the speaker 123 (refer to FIG. 3) provided for the earphones 10. The message may be, for example, "Turn on?"

After S11, the MPU 202 determines whether the user's response indicates that the operation is correct (S12). In the present exemplary embodiment, the user moves the muscles in his/her jaw or the like to respond. The user swallows saliva once to indicate "correct" and twice to indicate "incorrect". The number of times of swallowing is counted in a predetermined period of time.

The user may respond, however, through sound using a smart speaker, instead. In this case, the audio response from the user is obtained by the microphone 122 (refer to FIG. 3) provided for the earphones 10 and transmitted to the information terminal 20 as audio data. The MPU 202 analyzes the received audio response and determines whether to use the operation corresponding to the features of the brain wave information.

If a result of S12 is positive, the MPU 202 transmits the operation corresponding to the features of the brain wave information (S3).

If the result of S12 is negative, or if the result of S2 is negative, the MPU 202 determines whether the correspondence table 232 includes the features of the biological information other than brain waves (S4). The features of the biological information have been obtained in S1.

If the result of S4 is positive, the MPU 202 transmits the operation corresponding to the features of the biological information (S5).

If the result of S4 is negative, on the other hand, the MPU 202 ends the process.

Even when corresponding features are found in the correspondence table 231, an incorrect operation can be avoided by making the user check an operation as in the second process before an operation signal is transmitted to the operation target device 30.

With the second process, operation accuracy is expected to improve even in a period when the user's reproducibility of features of brain wave information is low.

Although the correspondence table 231 is used in the present exemplary embodiment, a learning model storing relationships between input features and output operations may be used, instead, as described in a later exemplary embodiment.

Results of Experiments

A fact that the earphones 10 (refer to FIG. 2) can obtain the user's brain wave information will be described hereinafter on the basis of results of an experiment conducted by a third party and results of an experiment conducted by the present applicant.

Reliability of MindWave (NeuroSky) in Comparison with Earphones 10

Figure 9:
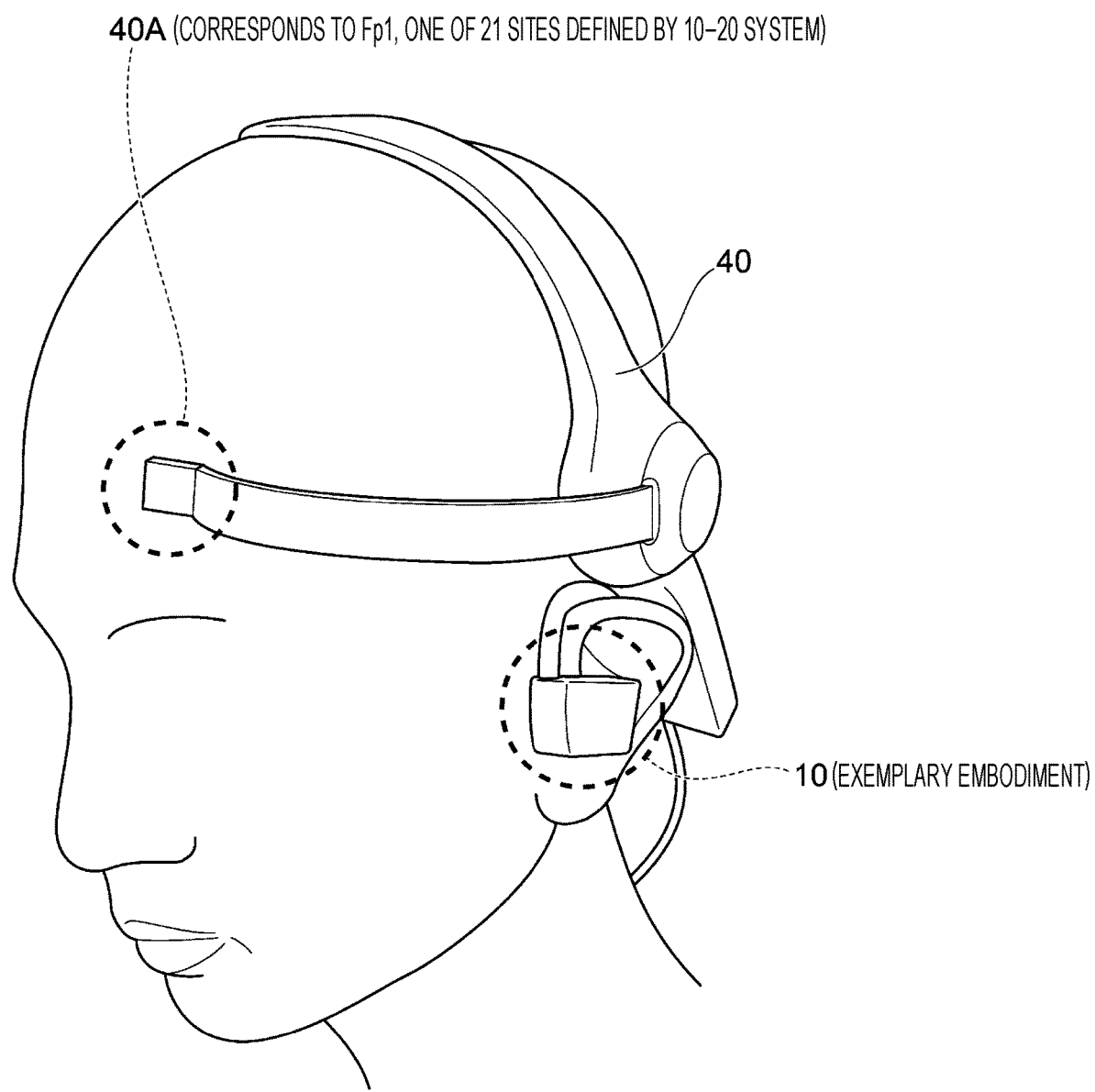
FIG. 9 is a diagram illustrating a measurement point of a headset equipped with a brain wave sensor capable of measuring brain waves with the earphones worn by the user.

FIG. 9 is a diagram illustrating a measurement point of a headset 40 equipped with a brain wave sensor capable of measuring brain waves with the earphones 10 worn by the user.

In this experiment, MindWave (registered trademark), which is manufactured by NeuroSky, Inc. and commercially available, is used as the headset 40 equipped with a brain wave sensor.

Whereas the earphones 10 use the external auditory meatuses as measurement points as described above, MindWave manufactured by NeuroSky Inc. uses a forehead 40A as a measurement point for brain waves.

The forehead 40A illustrated in FIG. 9 corresponds to Fp1, which is one of 21 sites specified in the 10-20 system recommended as an international standard of arrangement of electrodes for measuring brain waves.

Elena Ratti, et al., "Comparison of Medical and Consumer Wireless EEG Systems for Use in Clinical Trials" (https://www.frontiersin.org/articles/10.3389/fn-hum.2017.003 98/full) has verified that brain waves measured by MindWave are equivalent to ones measured by medically approved EEG systems.

This thesis has been reviewed by Dimiter Dimitrov, PhD, a senior scientist at Duke University, and Marta Parazzini, PhD, at Polytechnic University of Milan and the National Research Council (CNR) in Italy.

Figure 10:
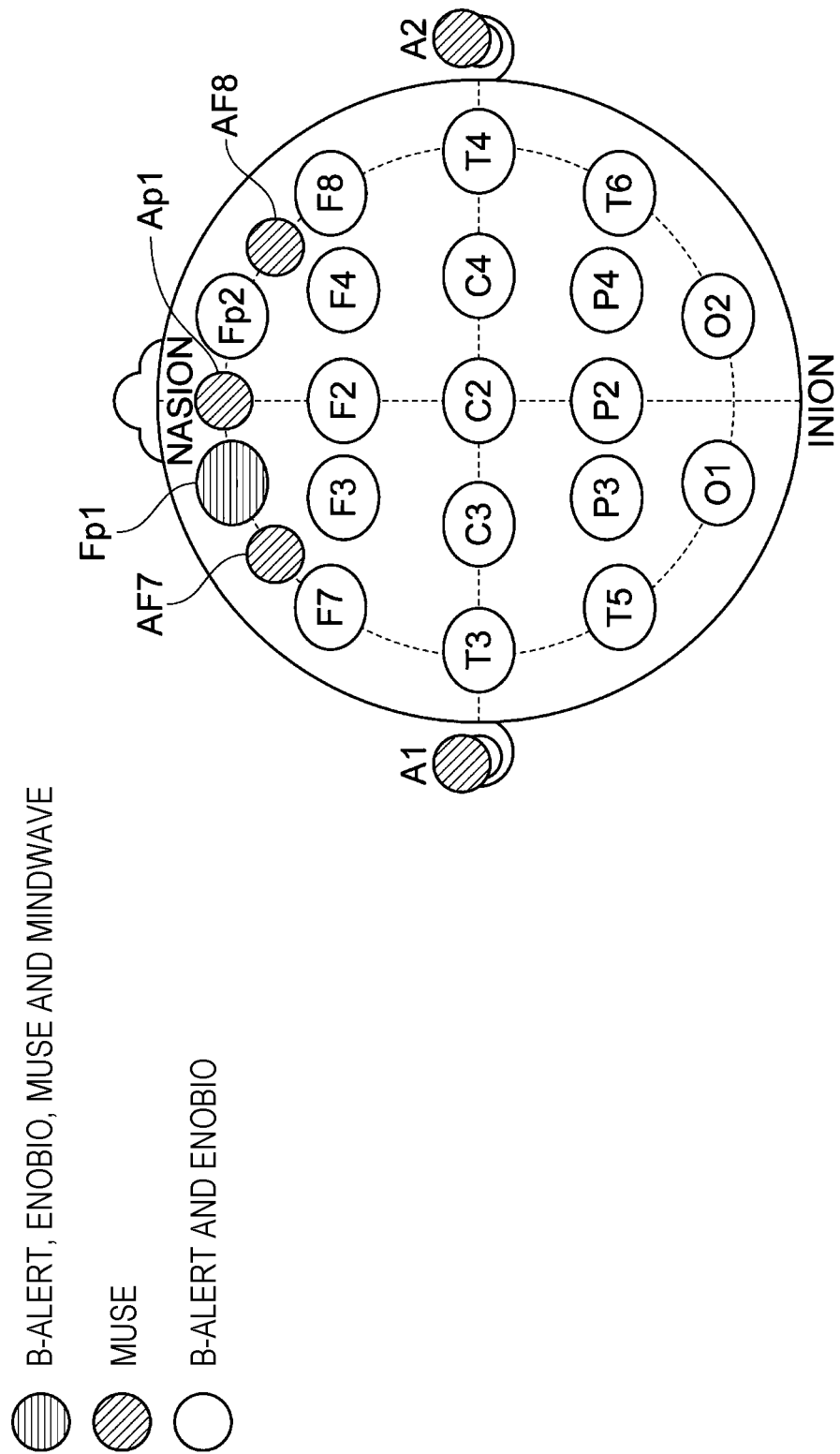
FIG. 10 is a diagram illustrating measurement points for brain waves described in a thesis.

FIG. 10 is a diagram illustrating measurement points for brain waves used in the thesis.

"B-Alert" (registered trademark) and "Enobio" in FIG. 10 are names of medically approved EEG systems in Europe and the U.S. "Muse" (registered trademark) and "MindWave" are names of consumer EEG systems.

In FIG. 10, sites indicated by hollow circles are measurement points used only by the medically approved EEG systems. Sites AF7, Ap1, AF8, A1, and A2, on the other hand, are measurement points used only by Muse, which is a consumer EEG system. Fp1 is a measurement point used by all the four EEG systems. That is, Fp1 is a measurement point of MindWave. The measurement points A1 and A2 are located between the auricles and the temples, not in the external auditory meatuses.

Details of the thesis will not be described here, but brain waves of five healthy subjects at rest are measured on two separate days. In this experiment, Fp1 on the forehead is used as a common measurement point, and brain wave patterns and power spectrum densities in an open eye state and a closed eye state are compared with each other. Evaluation in the thesis corresponds to evaluation of output α waves in the closed eye state.

In addition, in a "Conclusion" section of the thesis, it is described that power spectra measured by MindWave at Fp1 are substantially the same as with B-Alert and Enobio, which are the medically approved EEG systems, including results of reproduction tests, and peaks of α waves have been detected. It is also described that brain waves measured by MindWave include, as noise, blinking and movement in the open eye state. As a reason why the reliability of Muse is low, the thesis pointed out the possibility of an effect of artifacts.

Comparison between Results of Measurement with Earphones 10 and Results of Measurement with MindWave Results of an experiment in which brain waves have been measured with the subjects wearing the earphones 10 (refer to FIG. 9) or MindWave will be described hereinafter.

As illustrated in FIG. 9, the earphones 10 uses the exterior auditory meatuses as measurement points, and MindWave uses the forehead 40A as a measurement point.

In the experiment conducted by the present applicant, there are 58 subjects. Three attention enhancement tests and three meditation enhancement tests on the same day are designed for each subject, and α waves observed in the closed eye state are measured.

Although the actual number of subjects is 83, an effect of artifacts is excessive in results of measurement performed on 25 subjects, and these results are excluded.

In each attention enhancement test, the subjects are instructed to keep looking at a tip of a pen 150 mm away for 30 seconds with their eyes open. This test creates a concentrated state to suppress appearance of α waves and increase beta waves.

In each meditation enhancement test, the subjects are instructed to meditate for 30 seconds with their eyes closed. This test corresponds to evaluation of output α waves in the closed eye state. In other words, this test aims to detect the percentage of increase in α waves in a relaxed state.

In the experiment, the meditation enhancement test is conducted after the attention enhancement test, and output α waves are evaluated.

When output α waves are evaluated, a subject is usually instructed to keep his/her eyes open for 30 seconds and then keep his/her eyes closed for 30 seconds, and this process is repeated twice, and an increase in α waves in the closed eye state is detected.

In the present experiment, however, the number of sets is increased in order to collect a large amount of data.

First, a reason why the meditation enhancement tests are conducted and a method used in the evaluation of output α waves in the closed eye state will be described.

Figure 11:
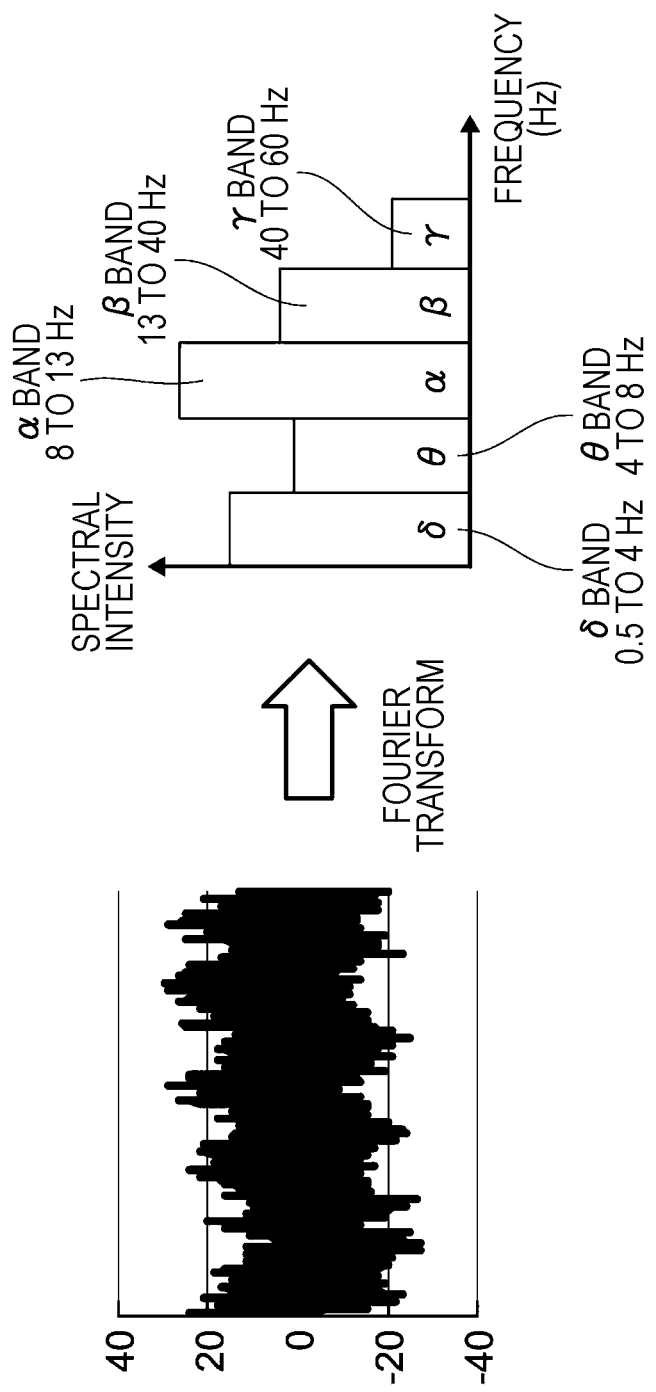
FIG. 11 is a diagram illustrating evaluation of output α waves.

FIG. 11 is a diagram illustrating the evaluation of output α waves. As illustrated in FIG. 11, raw data regarding brain waves can be roughly classified into delta waves, theta waves, α waves, beta waves, and gamma waves.

It is considered that the reproducibility of brain waves based on human motion is low and evaluation of the reproducibility of acquisition performance based on clinical data is difficult. α waves, however, tend to remain constant regardless of whether a person's eyes are open or closed.

Every type of brain wave tend to be observed in the open eye state, but every type of brain wave other than α waves tend to attenuate in the closed eye state. That is, α waves can be relatively easily observed without being affected even in the open eye state.

On the basis of this characteristic, raw data regarding brain waves in the experiment is subjected to a Fourier transform, and a spectral intensity Sn in a frequency band corresponding to each type of brain wave is determined as a feature value.

In the experiment, an α wave intensity ratio Tα is defined as a ratio (=Sα/ΣSn) of a spectral intensity Sα in an α band to the sum of spectral intensities in all the frequency bands (i.e., ΣSn), and whether the α wave intensity ratio Tα has increased in the closed eye state is determined.

If an increase in the α wave intensity ratio Tα is observed, it is proved that brain waves have been measured.

The comparison between the results of the measurement performed with the earphones 10 and the results of the measurement performed with MindWave will be described with reference to FIGS. 12A to 13B.

Figure 12A:
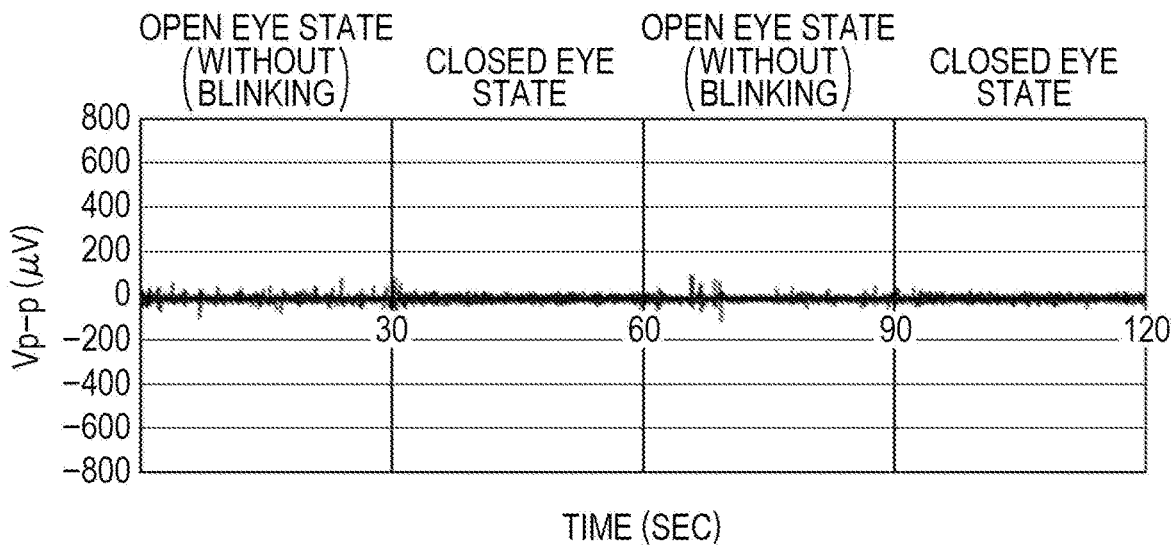
FIGS. 12A and 12B are diagrams illustrating results of measurement performed with MindWave.
Figure 12B:
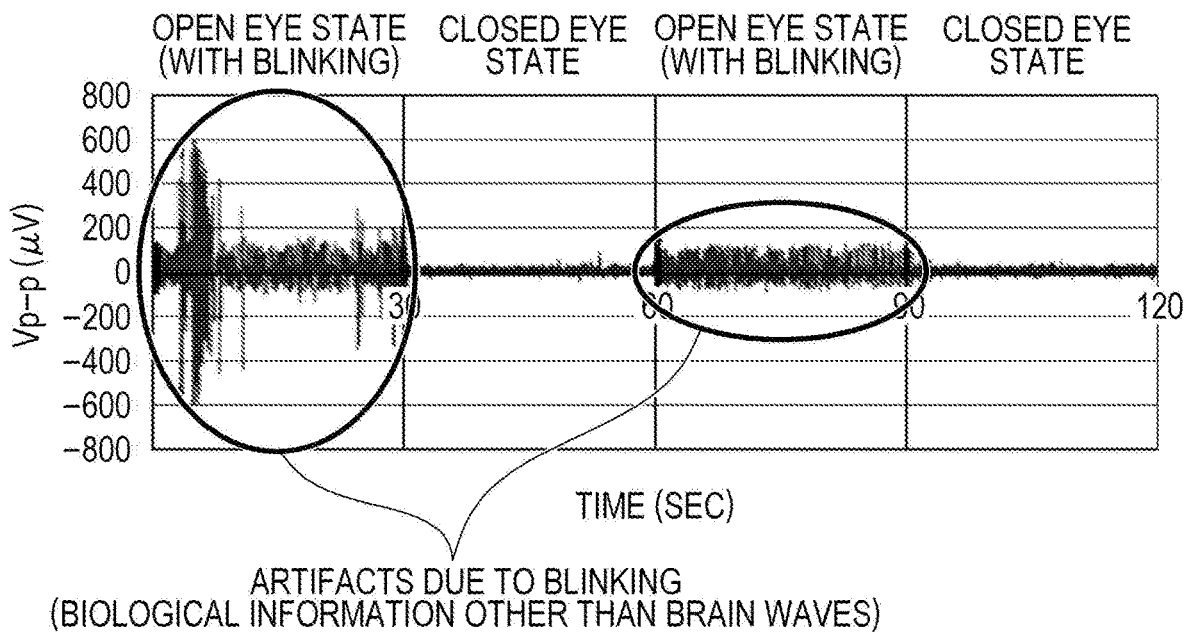

FIGS. 12A and 12B are diagrams illustrating the results of the measurement performed with MindWave. FIG. 12A illustrates a result of measurement at a time when the open eye state and the closed eye state are alternated twice without blinking, and FIG. 12B illustrates a result of measurement at a time when the open eye state and the closed eye state are alternated twice with blinking.

Figure 13A:
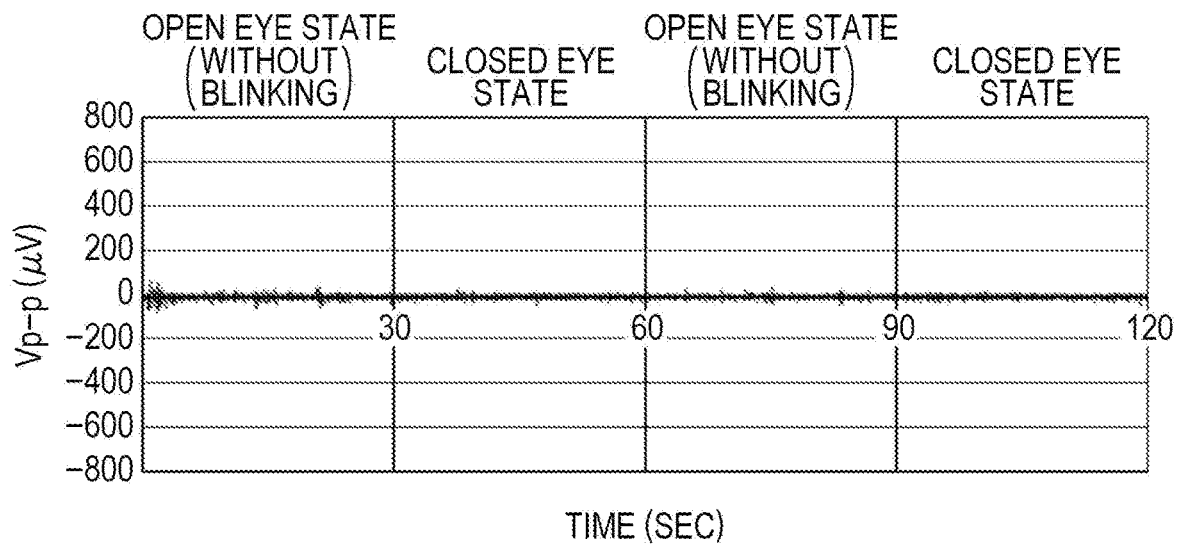
FIGS. 13A and 13B are diagrams illustrating results of measurement performed with the earphones used in the first exemplary embodiment.
Figure 13B:
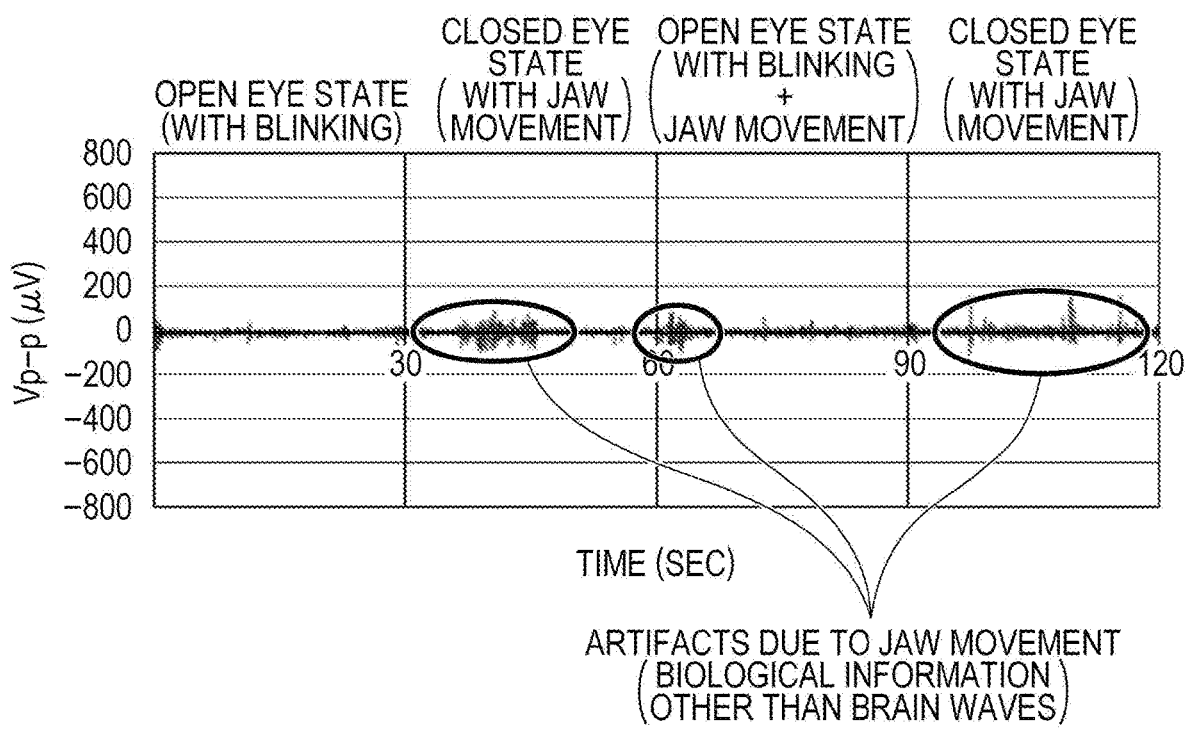

FIGS. 13A and 13B are diagrams illustrating the results of the measurement performed with the earphones 10 (refer to FIG. 2) used in the present exemplary embodiment. FIG. 13A illustrates a result of measurement at a time when the open eye state and the closed eye state are alternated twice without blinking, and FIG. 13B illustrates a result of measurement at a time when the open eye state and the closed eye state are alternated with blinking and movement of the jaw.

Without blinking, the result of the measurement performed with the earphones 10 and the result of the measurement performed with MindWave are closely similar to each other.

With blinking, however, artifacts caused by the blinking are evident in the results of the measurement performed with MindWave. This is probably because the forehead, which is used for measurement by MindWave, is close to the eyes and blinking in the open eye state tends to be detected as major artifacts. This has also been pointed out in the above-described thesis by Elena Ratti, et al.

Most of the artifacts due to blinking are observed in the delta band. When there are major artifacts as in FIG. 12, however, an increase in α waves might be erroneously detected. This is because as a result of an increase in the sum of the spectral intensities in all the frequency bands in the open eye state, the α wave intensity ratio Tα in the open eye state decreases, and the α wave intensity ratio Tα in the closed eye state looks relatively large. This is why the number of subjects has been reduced.

The artifacts caused by the blinking include not only potential variations derived from a living body due to movement of the eyelids but also potential variations derived from brain waves caused when the subjects try to move their eyelids.

In the result of the measurement performed with the earphones 10 (refer to FIG. 2) according to the present exemplary embodiment, on the other hand, artifacts due to blinking have not been described in a period of 0 to 30 seconds.

It has been confirmed, however, that artifacts due to a movement of the jaw for swallowing saliva are detected regardless of whether the subjects' eyes are open or closed. Most of the artifacts due to a movement of the jaw for swallowing saliva have been observed in the theta band.

The spectral intensity of the artifacts caused by swallowing of saliva, on the other hand, is much lower than that of the artifacts corresponding to blinking detected by MindWave. The spectral intensity of the artifacts caused by swallowing of saliva, therefore, has not affected an increase in α waves unlike in the case of MindWave.

The artifacts caused by swallowing of saliva, too, include not only potential variations derived from a living body in accordance with movement of the muscles in the jaw but also potential variations derived from brain waves caused when the subjects try to move the muscles in their jaws.

A reason why the movement of the jaw for swallowing saliva is taken as an example of the intentional movement of muscles while a user is desiring a certain operation in his/her mind in the above description is the occurrence of the artifacts illustrated in FIG. 13.

Next, an increase in α waves observed in the result of the measurement performed with the earphones 10 and an increase in α waves observed in the result of measurement performed with MindWave will be described with reference to FIG. 14A to FIG. 15C.

Figure 14A:
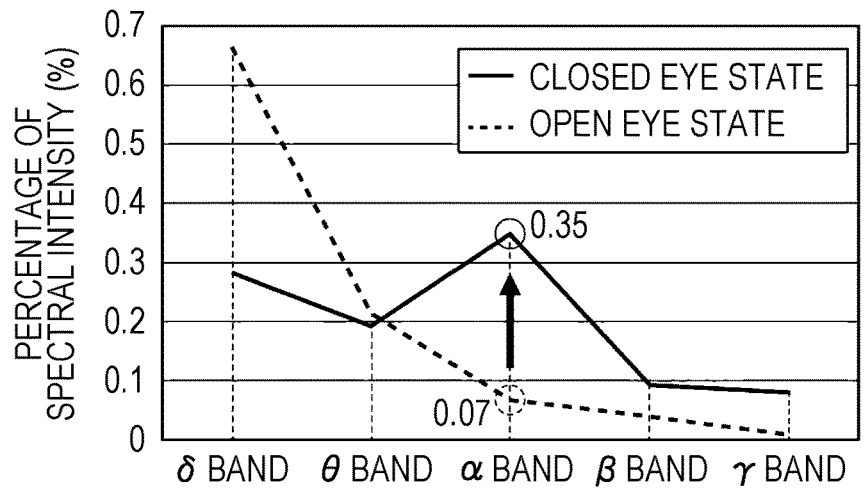
FIGS. 14A to 14C are diagrams illustrating other results of the measurement performed with MindWave.
Figure 14B:
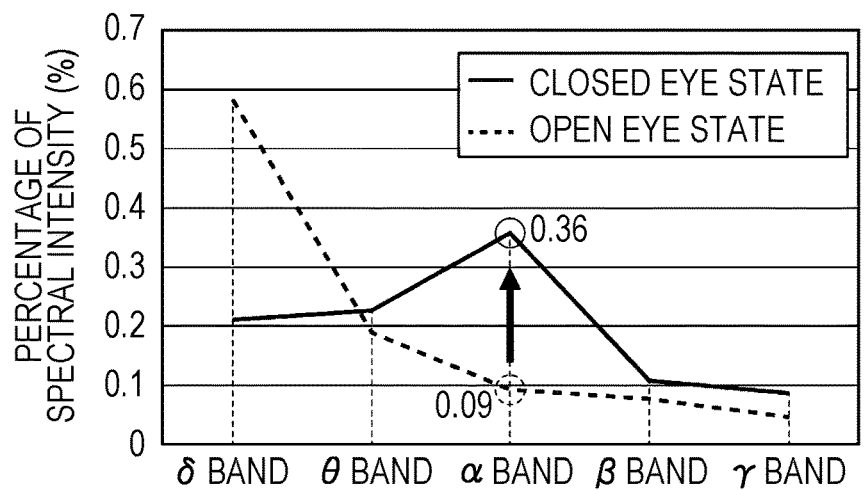
Figure 14C:
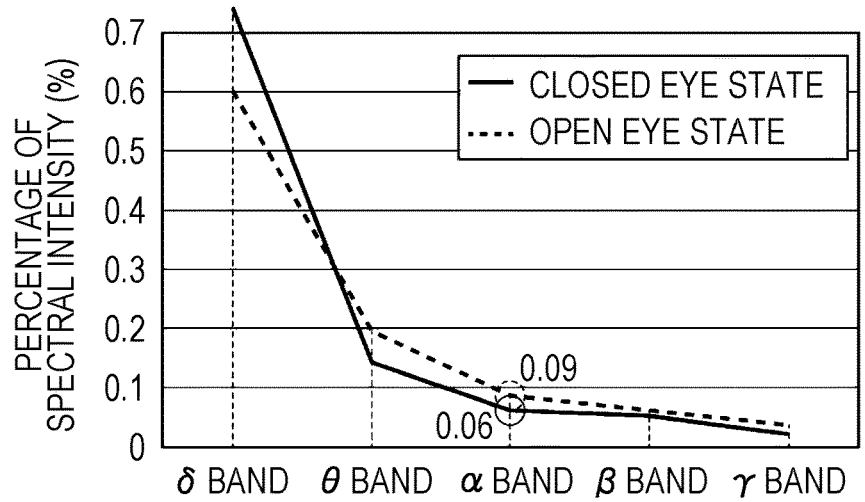

FIGS. 14A to 14C are diagrams illustrating other results of the measurement performed with MindWave. FIG. 14A illustrates changes in the percentage of spectral intensity in each frequency band at a time when the subjects have entered the closed eye state from the open eye state with blinking. FIG. 14B illustrates changes in the percentage of spectral intensity in each frequency band at a time when the subjects have entered the closed eye state from the open eye state without blinking. FIG. 14C illustrates a case where α waves do not increase.

Figure 15A:
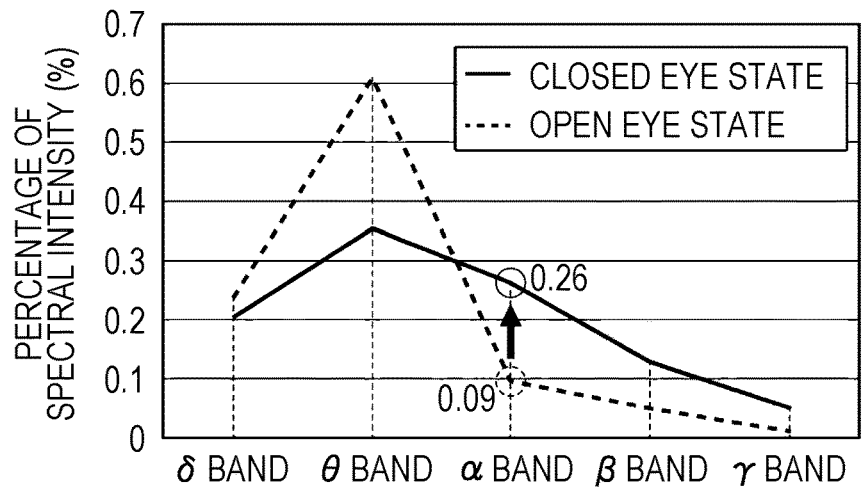
FIGS. 15A to 15C are diagrams illustrating other results of the measurement performed with the earphones used in the first exemplary embodiment.
Figure 15B:
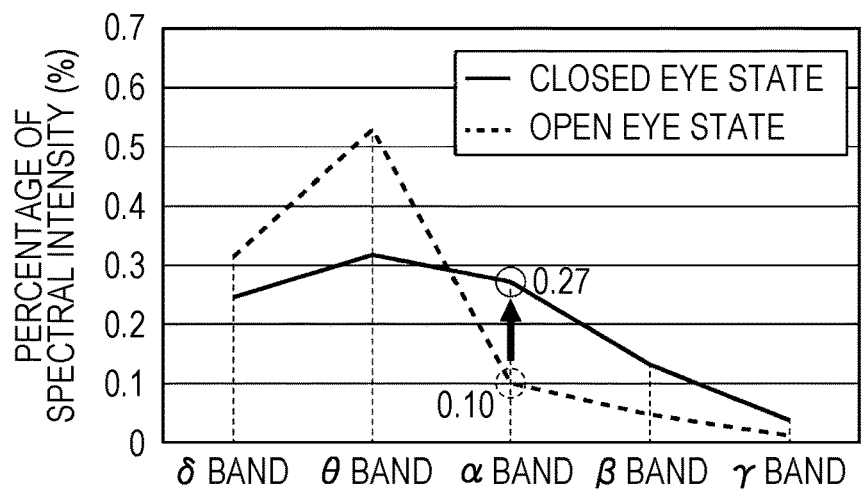
Figure 15C:
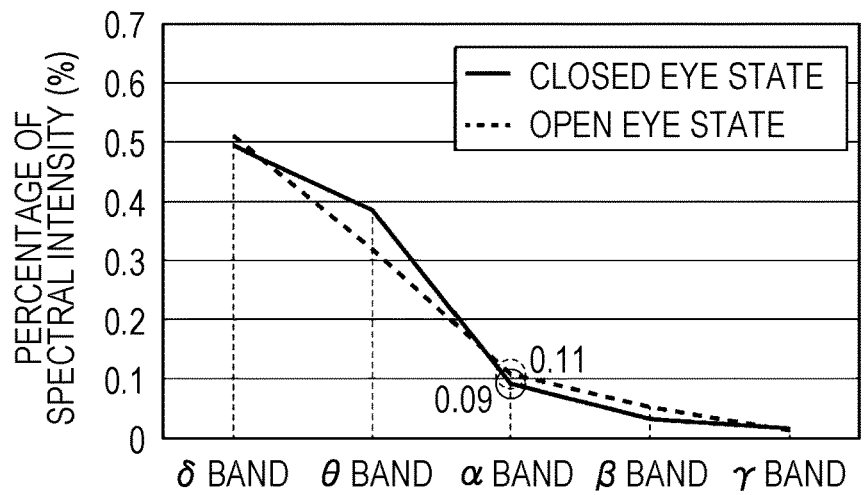

FIGS. 15A to 15C are diagrams illustrating the results of the measurement performed with the earphones 10 (refer to FIG. 2) used in the present exemplary embodiment. FIG. 15A illustrates changes in the percentage of spectral intensity in each frequency band at a time when the subjects have entered the closed eye state from the open eye state with blinking. FIG. 15B illustrates changes in the percentage of spectral intensity in each frequency band at a time when the subjects have entered the closed eye state from the open eye state without blinking. FIG. 15C illustrates a case where α waves do not increase.

Vertical axes in FIGS. 14A to 15C represent the percentage of spectral intensity, and horizontal axes represent the frequency bands. Subjects corresponding to FIG. 14A are the same as those corresponding to FIG. 15A. Similarly, subjects corresponding to FIG. 14B are the same as those corresponding to FIG. 15B, and subjects corresponding to FIG. 14C are the same as those corresponding to FIG. 15C.

The distribution of the spectral intensity of MindWave (refer to FIGS. 14A to 14C) and the distribution of the spectral intensity of the earphones 10 (refer to FIGS. 15A to 15C) are different from each other in low frequency bands of delta waves to theta waves, but the same in the α band and higher.

In the experiment, the number of subjects with whom an increase in α waves has been observed with both MindWave and the earphones 10 is 46, which is slightly less than 80% of the total number of subjects, namely 58.

The number of subjects with whom an increase in α waves has been observed only with the earphones 10 is seven. In other words, an increase in α waves has been observed with 53 subjects in the case of the earphones 10. That is, in the case of the earphones 10, an increase in α waves has been observed with slightly more than 90% of the total number of subjects.

The number of subjects with whom an increase in α waves has been observed with neither MindWave nor the earphones 10 is five. Waveforms illustrated in FIGS. 14C and 15C indicate results of measurement performed on the five subjects.

Figure 16A:
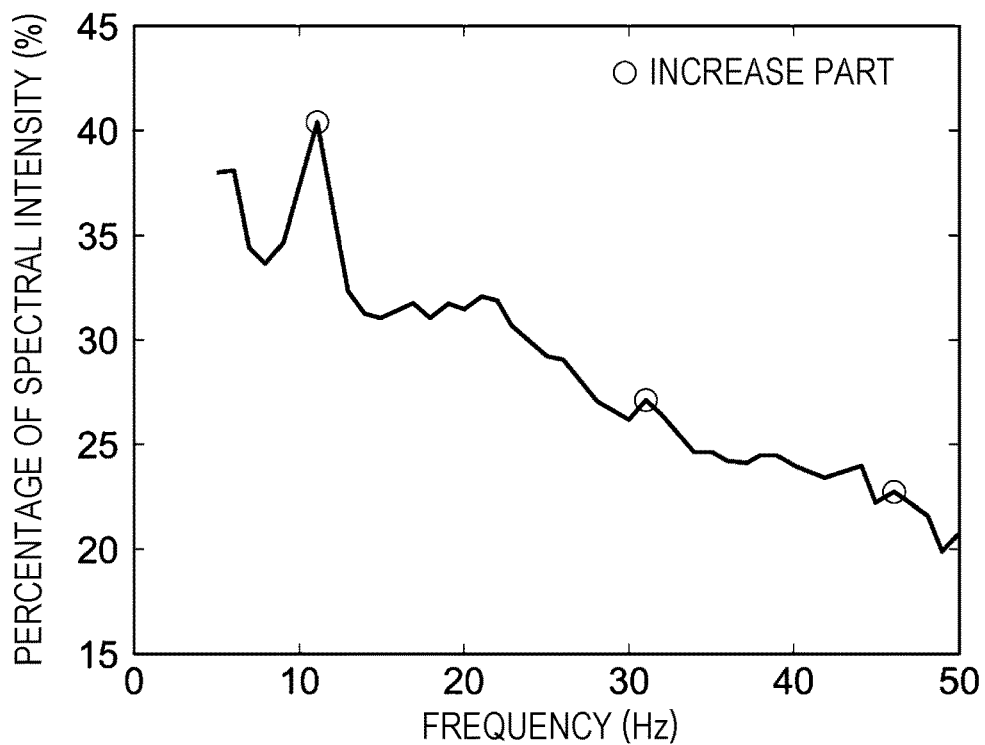
FIGS. 16A and 16B are diagrams illustrating an example of presentation of parts in which spectral intensity has increased.
Figure 16B:
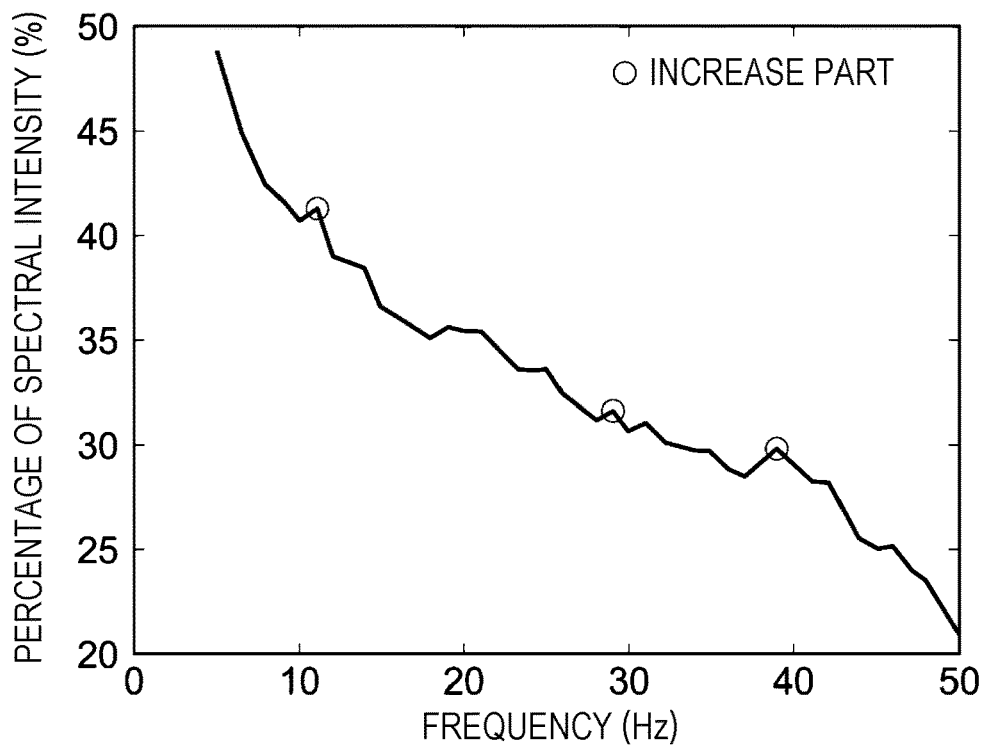

FIGS. 16A and 16B are diagrams illustrating an example of presentation of parts in which spectral intensity has increased. FIG. 16A illustrates a result of the measurement performed with MindWave, and FIG. 16B illustrates a result of the measurement performed with the earphones 10 (refer to FIG. 2) used in the present exemplary embodiment. Vertical axes represent the percentage of spectral intensity, and horizontal axes represent frequency.

In FIGS. 16A and 16B, unlike in FIGS. 14A to 15C, actual frequency is used for the horizontal axes. In the above-described thesis by Elena Ratti, et al., horizontal axes represent actual frequency to describe an increase in α waves. The parts in which spectral frequency has increased are indicated by hollow circles in FIGS. 16A and 16B.

As illustrated in FIGS. 16A and 16B, in either measurement method, the percentage of spectral intensity decreases as the frequency increases. This holds true in the thesis by Elena Ratti, et al.

It has thus been confirmed that the earphones 10 used in the present exemplary embodiment, which measure brain waves at the exterior auditory meatuses, has measurement capability equivalent to that of MindWave.

Second Exemplary Embodiment

In the first exemplary embodiment, correspondence between features and operations stored in the correspondence tables 231 and 232 (refer to FIGS. 6A and 6B) are defined in advance.

For this reason, it is difficult to operate the operation target device 30 (refer to FIG. 1) as intended unless the user wearing the earphones 10 correctly generates features of brain wave information. In addition, standardized correspondences might not be applicable to every user.

In a second exemplary embodiment, therefore, an example of a mechanism for updating correspondences through machine learning will be described.

Figure 17:
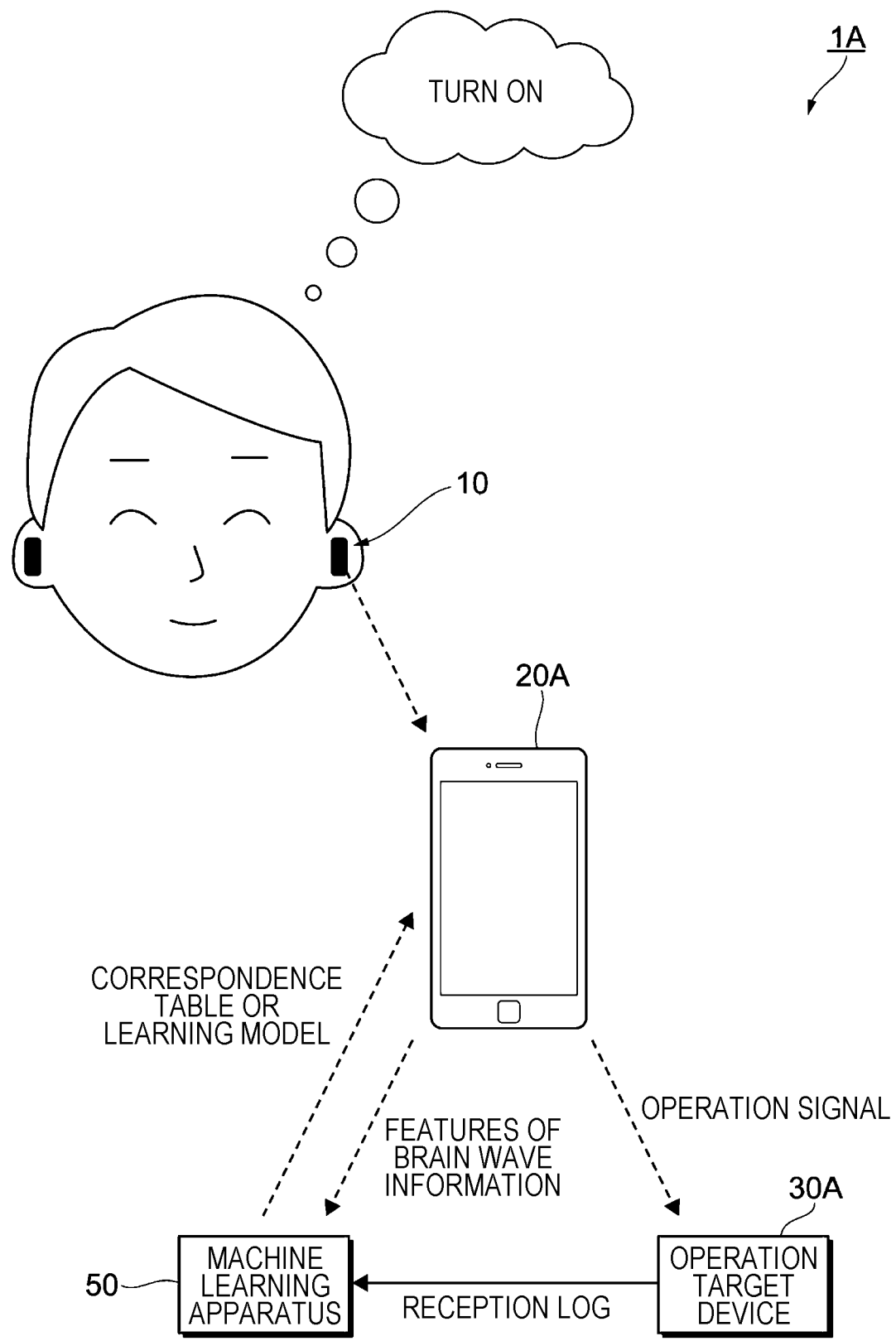
FIG. 17 is a diagram illustrating a schematic configuration of a brain wave operation system used in a second exemplary embodiment.

FIG. 17 is a diagram illustrating a schematic configuration of a brain wave operation system 1A used in the second exemplary embodiment. In FIG. 17, the same elements as in FIG. 1 are given the same reference numerals.

The brain wave operation system 1A illustrated in FIG. 17 includes the earphones 10 attached to the ears, an information terminal 20A wirelessly connected to the earphones 10, an operation target device 30A to be operated by the user, and a machine learning apparatus 50.

The operation target device 30A and the machine learning apparatus 50 are connected to each other over an IoT network. The machine learning apparatus 50 need not exist in the same space as the information terminal 20A and the operation target device 30A. The machine learning apparatus 50 may exist, for example, on the Internet.

The information terminal 20A according to the present exemplary embodiment has a function of transmitting features of brain wave information used to determine an operation signal to the machine learning apparatus 50. The information terminal 20A may also have a function of transmitting features of biological information other than brain waves to the machine learning apparatus 50.

The operation target device 30A according to the present exemplary embodiment has a function of transmitting a log (hereinafter referred to as a "reception log") of a received operation signal to the machine learning apparatus 50. The operation target device 30A may transmit a reception log each time the operation target device 30A receives an operation signal or only if the machine learning apparatus 50 requests a reception log.

The machine learning apparatus 50 according to the present exemplary embodiment compares features of brain wave information and reception logs with each other and mechanically learns relationships between the brain wave information and operations. The machine learning apparatus 50 extracts reception logs relating to times at which the information terminal 20A has transmitted operation signals and learns relationships between features of brain wave information and operations intended by users.

A method in which correct operations are used, for example, may be performed for the learning.

First, a correct operation needs to be identified. If the operation target device 30A keeps performing a received operation for a certain period of time or more immediately after an operation signal is transmitted, for example, the operation performed by the operation target device 30A is regarded as an operation intended by the user. If the information terminal 20A transmits an operation signal for turning off the operation target device 30A while the operation target device 30A is off, however, this operation is probably incorrect. In this case, the operation target device 30A should receive an operation signal for turning on the operation target device 30A after receiving the operation signal for turning off the operation target device 30A. If the operation target device 30A receives an opposite operation signal immediately after a time at which an operation signal has been transmitted, therefore, an operation corresponding to the opposite operation signal is regarded as an operation intended by the user.

Although operations intended by the user can be identified in accordance with predetermined rules like this, operations intended by the user when the user has operated the operation target device 30A through brain waves may be determined using a model obtained through machine learning based on reception logs, instead. Alternatively, the user may transmit correct operations to the machine learning apparatus 50 through the information terminal 20A.

In any case, the machine learning apparatus 50 performs so-called supervised learning using pairs of an identified operation and a corresponding set of features of brain wave information. A method of deep learning is used for the learning. Long short-term memory (LSTM) blocks may be introduced to hidden layers. Convolutional layers or pooling layers may also be added as hidden layers.

The machine learning apparatus 50 learns correspondences between features of brain wave information and operations through machine learning and transmits a result of the machine learning to the information terminal 20A as a correspondence table or a learning model.

Figure 18:
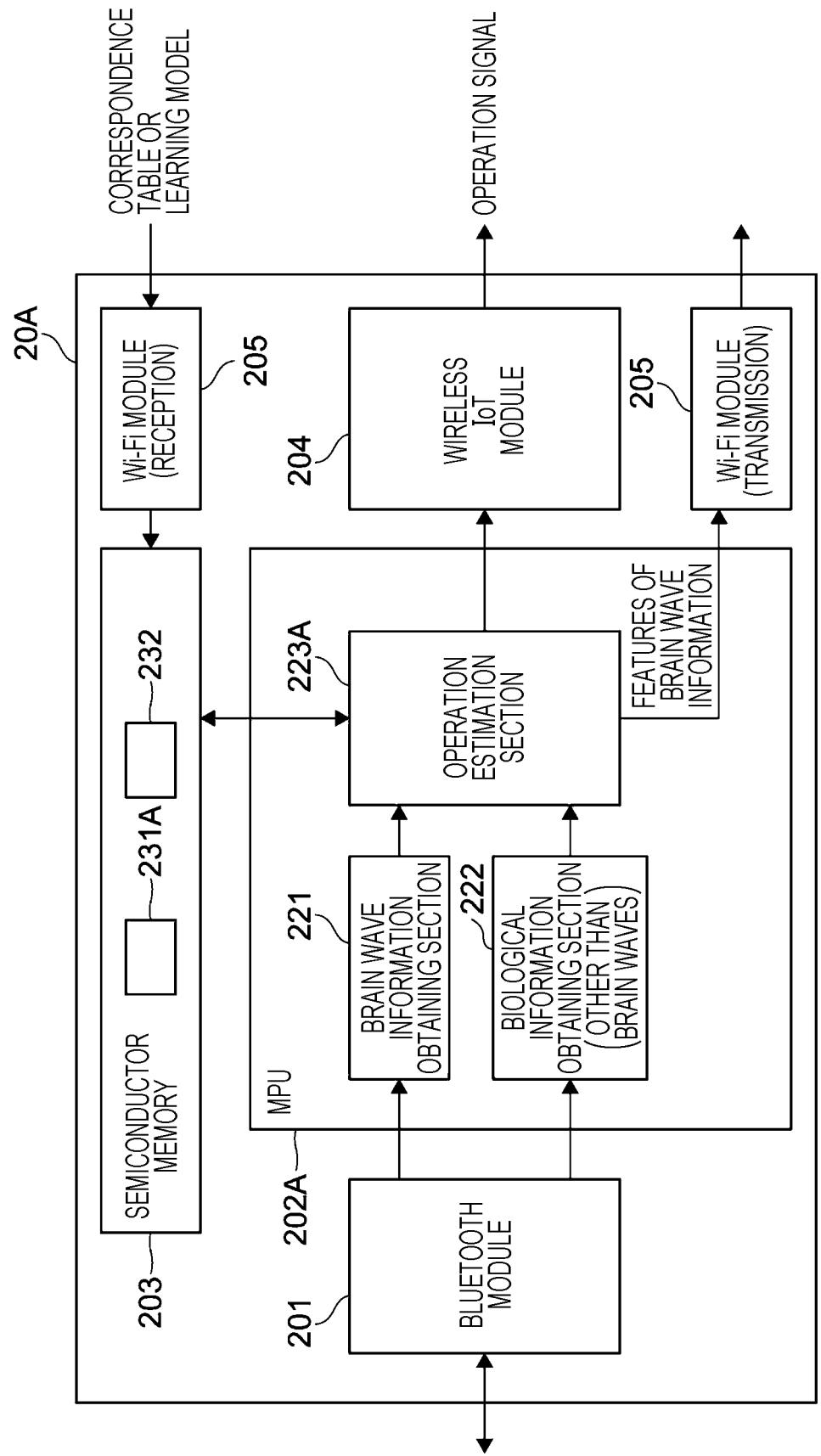
FIG. 18 is a diagram illustrating an example of the internal configuration of an information terminal used in the second exemplary embodiment.

FIG. 18 is a diagram illustrating an example of the internal configuration of the information terminal 20A used in the second exemplary embodiment. In FIG. 18, the same components as in FIG. 4 are given the same reference numerals.

FIG. 18, too, illustrates only devices of the information terminal 20A relating to a function of generating an operation signal for operating the operation target device 30A (refer to FIG. 17) from biological information such as brain waves.

In the case of the information terminal 20A illustrated in FIG. 18, a function of transmitting features of brain wave information used to estimate an operation signal to the machine learning apparatus 50 (refer to FIG. 17) is added to an operation estimation section 223A.

The information terminal 20A is also provided with a Wi-Fi (registered trademark) module 205 for communication with the machine learning apparatus 50. The Wi-Fi module 205 is used to transmit features of brain wave information to the machine learning apparatus 50 and receive a correspondence table or a learning model from the machine learning apparatus 50. The learning model stores correspondences between input features of brain wave information and output operations.

In FIG. 18, the semiconductor 203 stores a correspondence table 231A for features of brain wave information received from the machine learning apparatus 50. It is needless to say that the semiconductor 203 may store a learning model instead of the correspondence table 231A.

In the case of the brain wave operation system 1A according to the present exemplary embodiment, relationships between features of brain wave information caused in relation to operations performed by the user wearing the earphones 10 (refer to FIG. 17) through brain waves and operations are learned through machine learning, and the accuracy of correspondences between features of brain wave information and operations stored in the correspondence table 231A improves.

As a result, when machine learning is performed without identifying users, the accuracy of operations performed, through brain waves, by unspecified users wearing the earphones 10 capable of measuring brain waves improves.

When machine learning is performed with certain users, on the other hand, the accuracy of operations based on brain waves improves thanks to a correspondence table 231 or a learning model specific to the certain users.

Third Exemplary Embodiment

Although the operation target device 30A (refer to FIG. 17) is connected to the machine learning apparatus 50 (refer to FIG. 17) over an IoT network in the second exemplary embodiment, a case where the operation target device 30A is not connected to the machine learning apparatus 50 (refer to FIG. 17) over an IoT network or the like will be described in a third exemplary embodiment.

Figure 19:
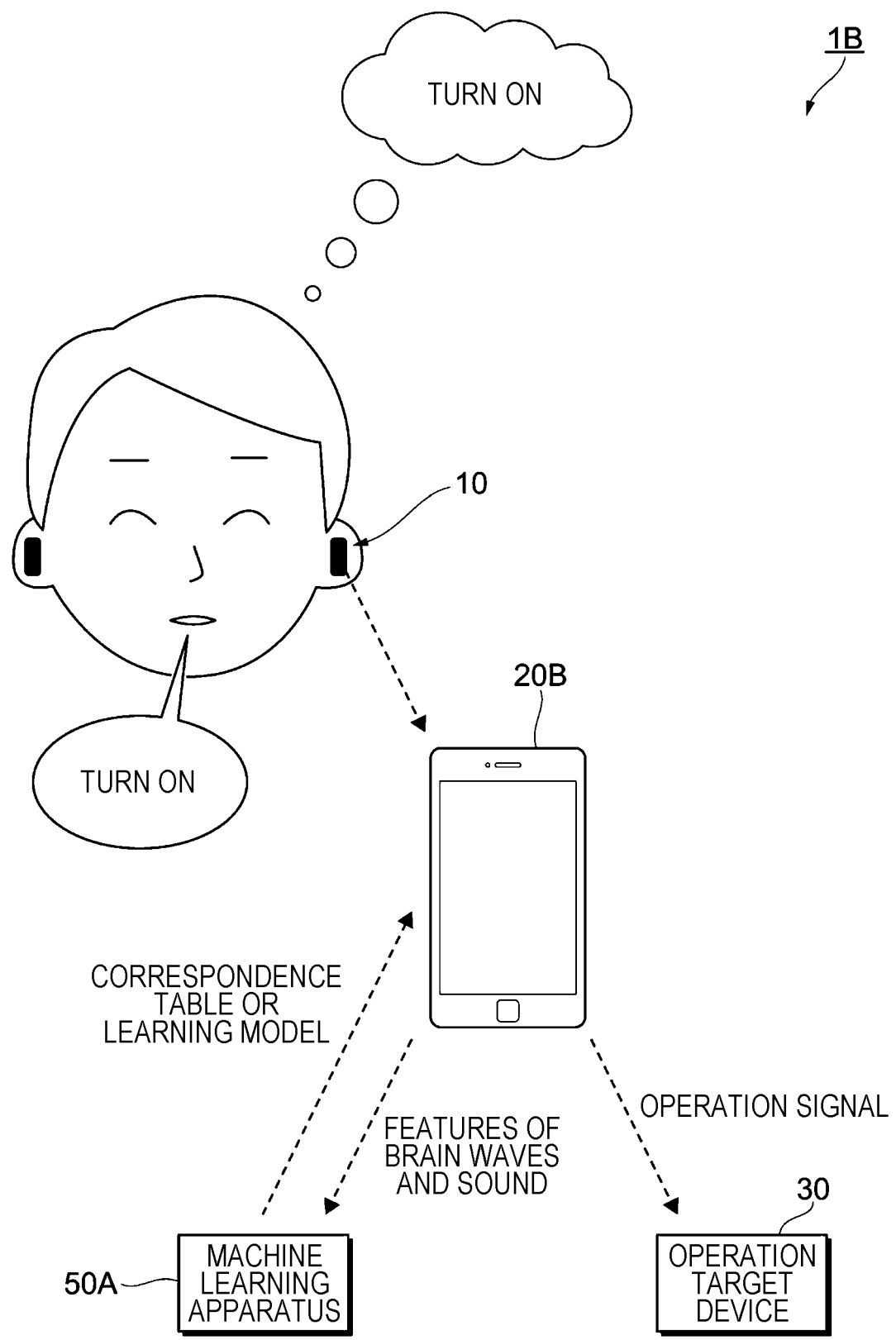
FIG. 19 is a diagram illustrating a schematic configuration of a brain wave operation system used in a third exemplary embodiment.

FIG. 19 is a diagram illustrating a schematic configuration of a brain wave operation system 1B used in the third exemplary embodiment. In FIG. 19, the same components as in FIG. 17 are given the same reference numerals.

The brain wave operation system 1B illustrated in FIG. 19 includes the earphones 10 attached to the ears, an information terminal 20B wirelessly connected to the earphones 10, the operation target device 30 to be operated by the user, and a machine learning apparatus 50A.

In the present exemplary embodiment, the machine learning apparatus 50A obtains information regarding correct operations through sounds uttered by the user. The information terminal 20B therefore has a function of analyzing a sound obtained by the microphone 122 (refer to FIG. 3) and transmitting a result of the analysis to the machine learning apparatus 50A.

The machine learning apparatus 50A may analyze a sound, instead. A sound recognition service provided through a server on the Internet or the like may be used to analyze a sound.

In FIG. 19, the user utters a sound corresponding to "turn on", which is also being desired by the user in his/her mind. Although the whole operation looks the same as one achieved using a smart speaker because the operation target device 30 is operated in accordance with an operation orally requested by the user, a sound uttered by the user in the present exemplary embodiment is given as a correct operation estimated from with features of brain wave information.

Figure 20:
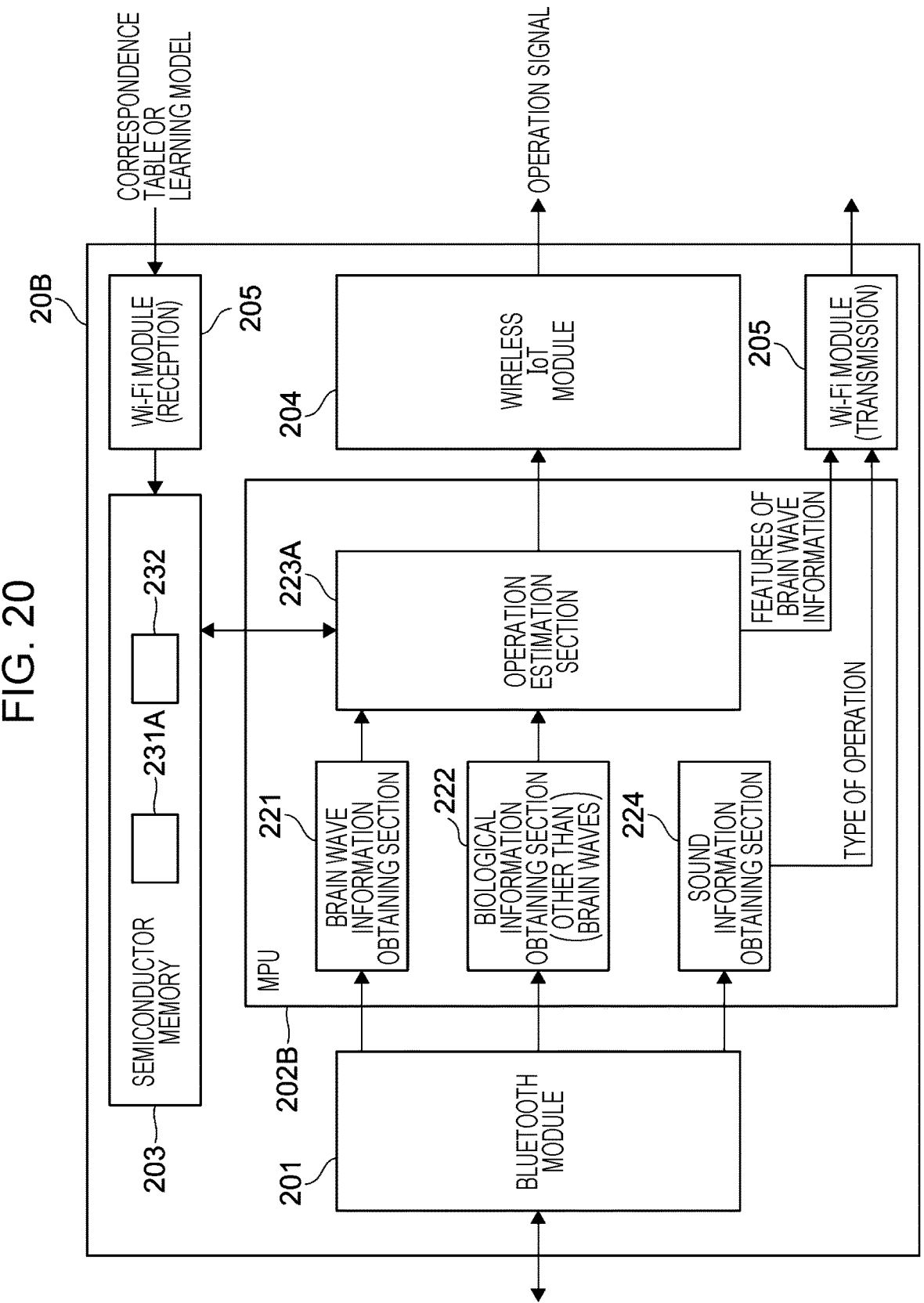
FIG. 20 is a diagram illustrating an example of the internal configuration of an information terminal used in the third exemplary embodiment.

FIG. 20 is a diagram illustrating an example of the internal configuration of the information terminal 20B used in the third exemplary embodiment. In FIG. 20, the same components as in FIG. 18 are given the same reference numerals.

FIG. 20, too, illustrates only devices of the information terminal 20B relating to a function of generating an operation signal for operating the operation target device 30 from biological information such as brain waves.

A sound information obtaining section 224 that obtains an operation from audio data received through the Bluetooth module 201 is added to the information terminal 20B illustrated in FIG. 20.

The sound information obtaining section 224 used in the present exemplary embodiment performs a process for analyzing a sound and outputting an operation.

When the machine learning apparatus 50A or an external sound recognition service is used, the sound information obtaining section 224 transmits obtained audio data to the machine learning apparatus 50A or the external sound recognition service.

In the brain wave operation system 1B according to the present exemplary embodiment, an oral instruction given by the user can be used as a correct operation based on brain waves, and a processing load is smaller than when a correct operation is estimated using a reception log.

In addition, since a correct operation is given as a sound, the accuracy of training data improves, which accordingly improves the accuracy of machine learning in the present exemplary embodiment.

Fourth Exemplary Embodiment

Figure 21:
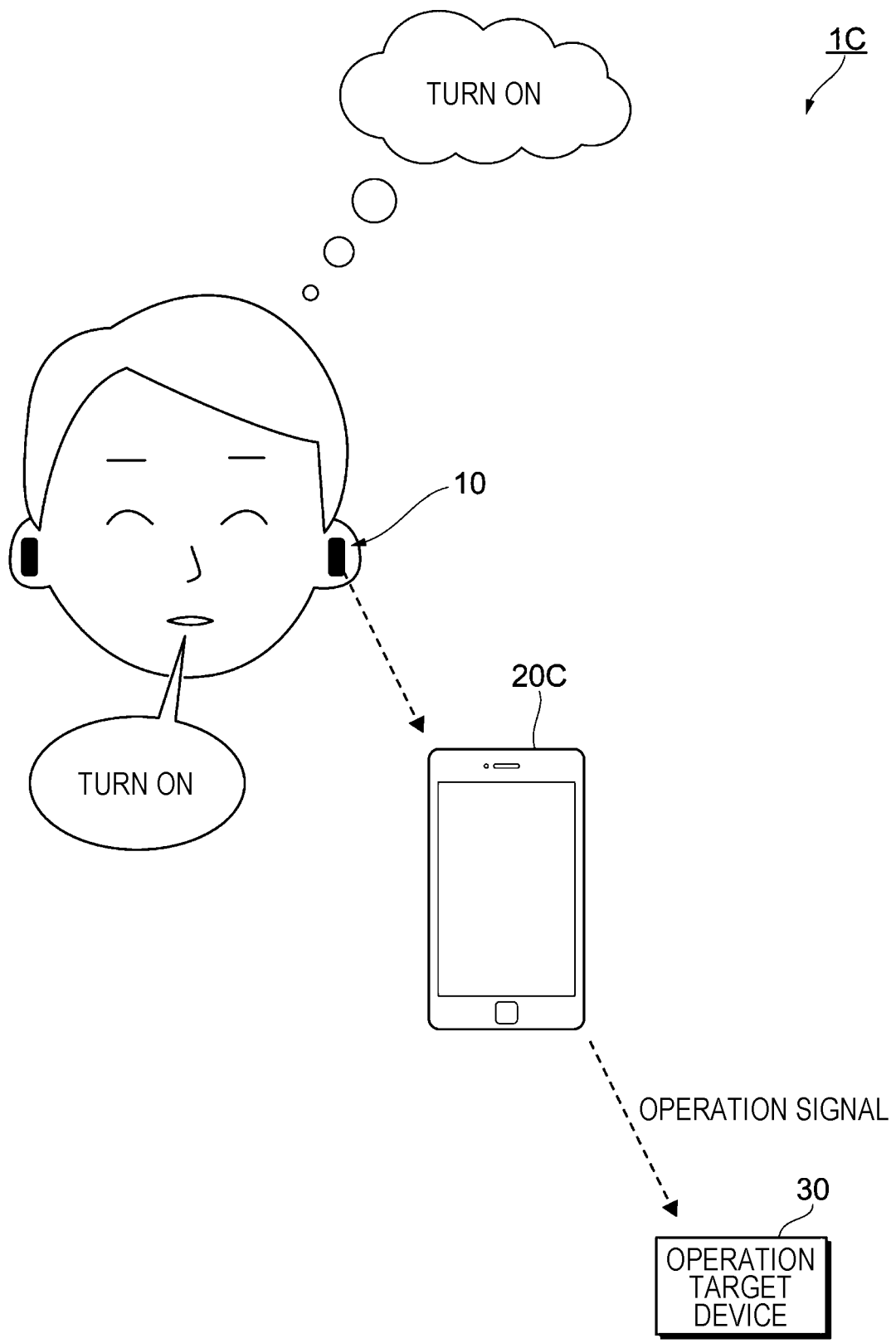
FIG. 21 is a diagram illustrating a schematic configuration of a brain wave operation system used in a fourth exemplary embodiment.

FIG. 21 is a diagram illustrating a schematic configuration of a brain wave operation system 1C used in a fourth exemplary embodiment. In FIG. 21, the same components as in FIG. 19 are given the same reference numerals.

In the present exemplary embodiment, machine learning is performed inside an information terminal 20C.

Figure 22:
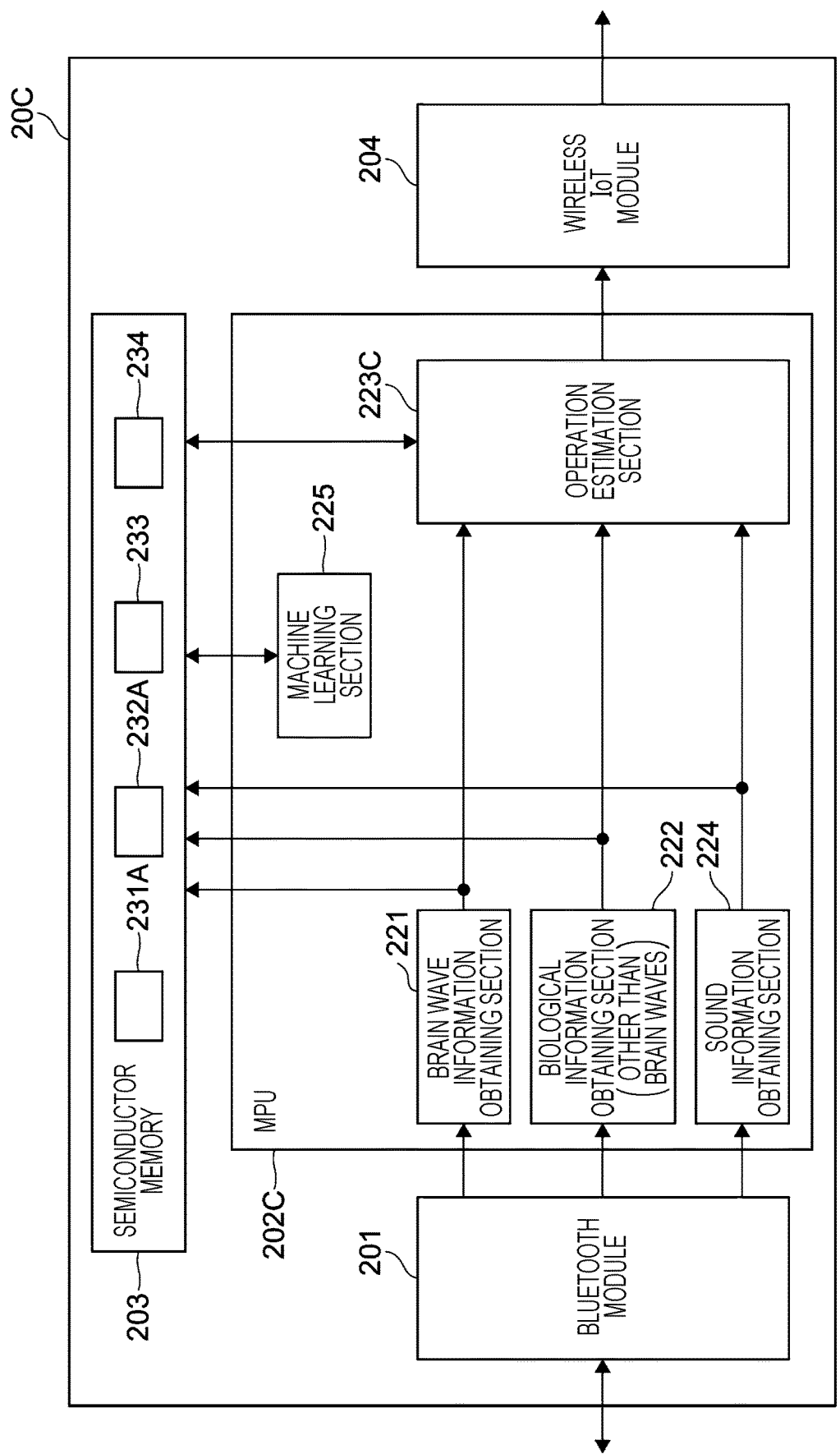
FIG. 22 is a diagram illustrating an example of the internal configuration of an information terminal used in the fourth exemplary embodiment.

FIG. 22 is a diagram illustrating an example of the internal configuration of the information terminal 20C according to the fourth exemplary embodiment. In FIG. 22, the same components as in FIG. 20 are given the same reference numerals.

A machine learning section 225 is added to the information terminal 20C illustrated in FIG. 22 as a function of an MPU 202C. The machine learning section 225 is provided by executing a program using the MPU 202C.

In addition, in the present exemplary embodiment, tables 233 and 234 storing a history of operations based on brain waves and information indicating whether the operations are correct are added to the semiconductor 203. The table 233 stores features of brain wave information, and the table 234 stores biological information other than brain waves.

The machine learning section 225 according to the present exemplary embodiment performs machine learning using the information stored in the table 233 as training data to update the correspondence table 231A for features of brain wave information. Similarly, the machine learning section 225 performs machine learning using the information stored in the table 234 as training data to update a correspondence table 232A for features of biological information other than brain waves.

The sound information obtaining section 224 according to the present exemplary embodiment, too, performs a process for analyzing a sound and outputting an operation. When an external sound recognition service is used, the sound information obtaining section 224 transmits obtained audio data to the external sound recognition service and obtains an operation as a result of an analysis conducted by the external sound recognition service. In either case, the operation is stored in the table 233 of the semiconductor 203.

If the accuracy of an operation estimated from features of brain wave information or features of biological information other than brain waves is low, an operation estimation section 223C according to the present exemplary embodiment transmits an orally requested operation to the operation target device 30.

FIGS. 23A and 23B are diagrams illustrating an example of the tables 233 and 234 storing a history of operations and information indicating whether the operations are correct. FIG. 23A illustrates the table 233 storing a history of operations estimated from features of brain wave information and information indicating whether the operations are correct, and FIG. 23B illustrates the table 234 storing a history of operations estimated from features of biological information other than brain waves and information indicating whether the operations are correct.

The table 233 stores times at which operations based on brain waves have been performed, features of brain wave information, estimated operations, operations indicated by sounds uttered by the user as the user's intention, and information indicating whether operations associated with the features are correct.

In FIG. 23A, it is indicated that an operation estimated from features of brain wave information at 12:45:52 on 10/15/20XX is the same as an operation indicated by a sound uttered by the user. The estimated operation is therefore "correct".

An operation estimated from features of brain wave information at 12:46:10 on 10/15/20XX, on the other hand, is different from an operation indicated by a sound uttered by the user. The estimated operation is therefore "incorrect".

The table 234 stores times at which operations based on brain waves have been performed, features of biological information other than brain waves, estimated operations, operations indicated by sounds uttered by the user as the user's intention, and information indicating whether operations associated with the features are correct.

Operations estimated from features of biological information other than brain waves at 12:45:52 and 12:46:10 on 10/15/20XX are the same as operations indicated by sounds uttered by the user. The estimated operations are therefore "correct".

The machine learning section 225 (refer to FIG. 22) according to the present exemplary embodiment keeps performing machine learning using the history stored in the table 233 as training data to update the correspondence table 231A for features of brain wave information. The machine learning section 225 also keeps performing machine learning using the history stored in the table 234 as training data to update the correspondence table 232A for features of biological information other than brain waves. When a learning model is stored instead of the correspondence table 231A, the learning model stored in the semiconductor 203 is updated using a learning model updated through machine learning.

Next, an example of a process performed by the information terminal 20C (refer to FIG. 21) by executing a program using the MPU 202C (refer to FIG. 22) will be described.

Figure 24:
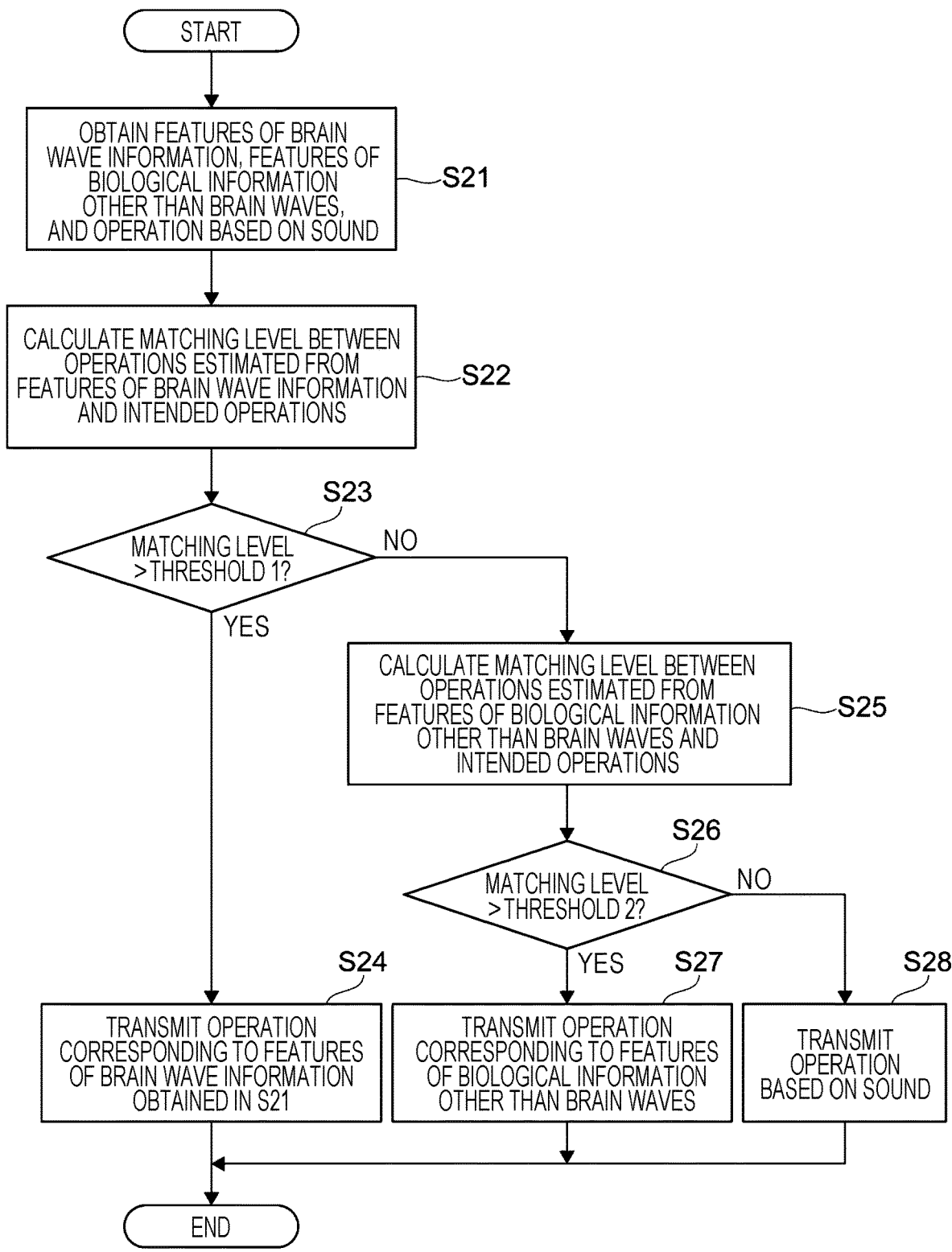
FIG. 24 is a flowchart illustrating an example of a process performed by the information terminal after the information terminal receives a digital signal including brain wave information.

FIG. 24 is a flowchart illustrating an example of a process performed by the information terminal 20C after the information terminal 20C receives a digital signal including brain wave information. "S" in FIG. 24 denotes a step.

Upon receiving a digital signal including brain wave information from the earphones 10 (refer to FIG. 21), the MPU 202C obtains, from the received digital signal, features of brain wave information, features of biological information other than brain waves, and an operation indicated by a sound (S21).

Next, the MPU 202C refers to the table 233 (refer to FIG. 23A) and calculates a matching level between operations estimated from features of brain wave information and intended operations (S22). The matching level may be calculated only on the basis of features similar to the features of brain wave information obtained in S21 or all samples in the past.

The matching level may be calculated while specifying a certain period of time. This is because, even when a matching level of latest samples is high, for example, an operation based on brain waves might not be achieved if a large number of past samples whose matching level is low are included. The matching level may be calculated, therefore, while limiting a period of time in which samples used for the calculation have appeared.

Next, the MPU 202C compares the calculated matching level with threshold 1 (S23). Threshold 1 is, say, 90%. This percentage, however, is just an example. In addition, the user may change threshold 1. Threshold 1 is an example of a first threshold.

When the number of samples is small, the accuracy of the estimation of an operation based on the current features of the brain wave information is not assured even if the matching level is high. When the number of samples is smaller than a predetermined value, therefore, a negative result may be automatically output.

If a result of S23 is positive, the MPU 202C transmits the operation corresponding to the features of the brain wave information (S24). This is a state in which the operation target device 30 (refer to FIG. 21) can be accurately operated through brain waves.

If the result of S23 is negative, on the other hand, the MPU 202C according to the present exemplary embodiment calculates a matching level between operations estimated from features of biological information other than brain waves and intended operations (S25).

Although an operation estimated from features of biological information other than brain waves is assumed to be correct in the first exemplary embodiment, an operation estimated from obtained features of biological information can be incorrect in the present exemplary embodiment. A case where the movement of the jaw for swallowing saliva is not large enough and a case where a movement of muscles from which features can be hardly obtained is used for performing an operation, for example, are also assumed.

This matching level, too, may be calculated only on the basis of features similar to the features of the biological information other than brain waves obtained in S21 or all the samples in the past.

A period of time to which samples belong, which is used to calculate the matching level, may be determined as a period of time used to calculate the matching level as in the case of the features of the brain wave information.

Next, the MPU 202C compares the calculated matching level with threshold 2 (S26). Threshold 2 is, say, 95%. Because the features of the biological information other than brain waves are based on a movement of muscles that can be intentionally moved by the user, threshold 2 may be higher than threshold 1 used in S23. The percentage, however, is just an example, and the user may be change threshold 2. Threshold 2 is an example of a second threshold.

If a result of S26 is positive, the MPU 202C transmits an operation corresponding to the features of the biological information other than brain waves (S27).

If the result of S26 is negative, on the other hand, the MPU 202C transmits the operation indicated by the sound (S28).

Because the brain wave operation system 1C according to the present exemplary embodiment, too, can use an oral instruction given by the user as a correct operation based on brain waves, the accuracy of training data improves, which accordingly improves the accuracy of machine learning.

In addition, because correspondences between features of brain wave information and operations can be learned while associating the correspondences with an account of the user wearing the earphones 10 (refer to FIG. 21) in the present exemplary embodiment, the correspondence tables 231A and 232A can be adjusted to the user. Consequently, the accuracy of the user's operations based on brain waves improves.

Fifth Exemplary Embodiment

Figure 25:
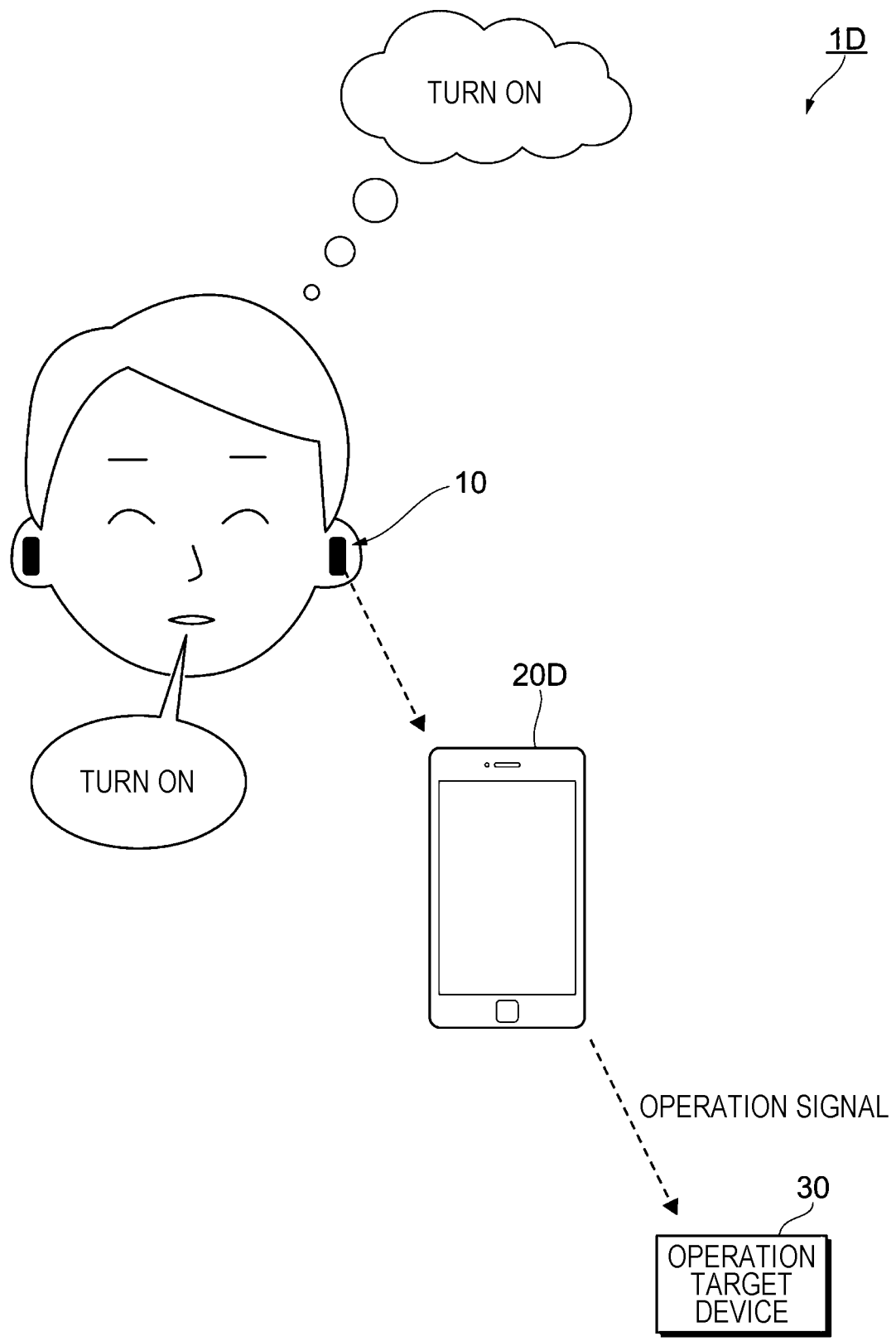
FIG. 25 is a diagram illustrating a schematic configuration of a brain wave operation system used in a fifth exemplary embodiment.

FIG. 25 is a diagram illustrating a schematic configuration of a brain wave operation system 1D used in a fifth exemplary embodiment. In FIG. 25, the same components as in FIG. 21 are given the same reference numerals.

The present exemplary embodiment is the same as the fourth exemplary embodiment in that the process of machine learning is performed inside an information terminal 20D.

The present exemplary embodiment, however, is different from the fourth exemplary embodiment in terms of a process performed to estimate an operation.

Figure 26:
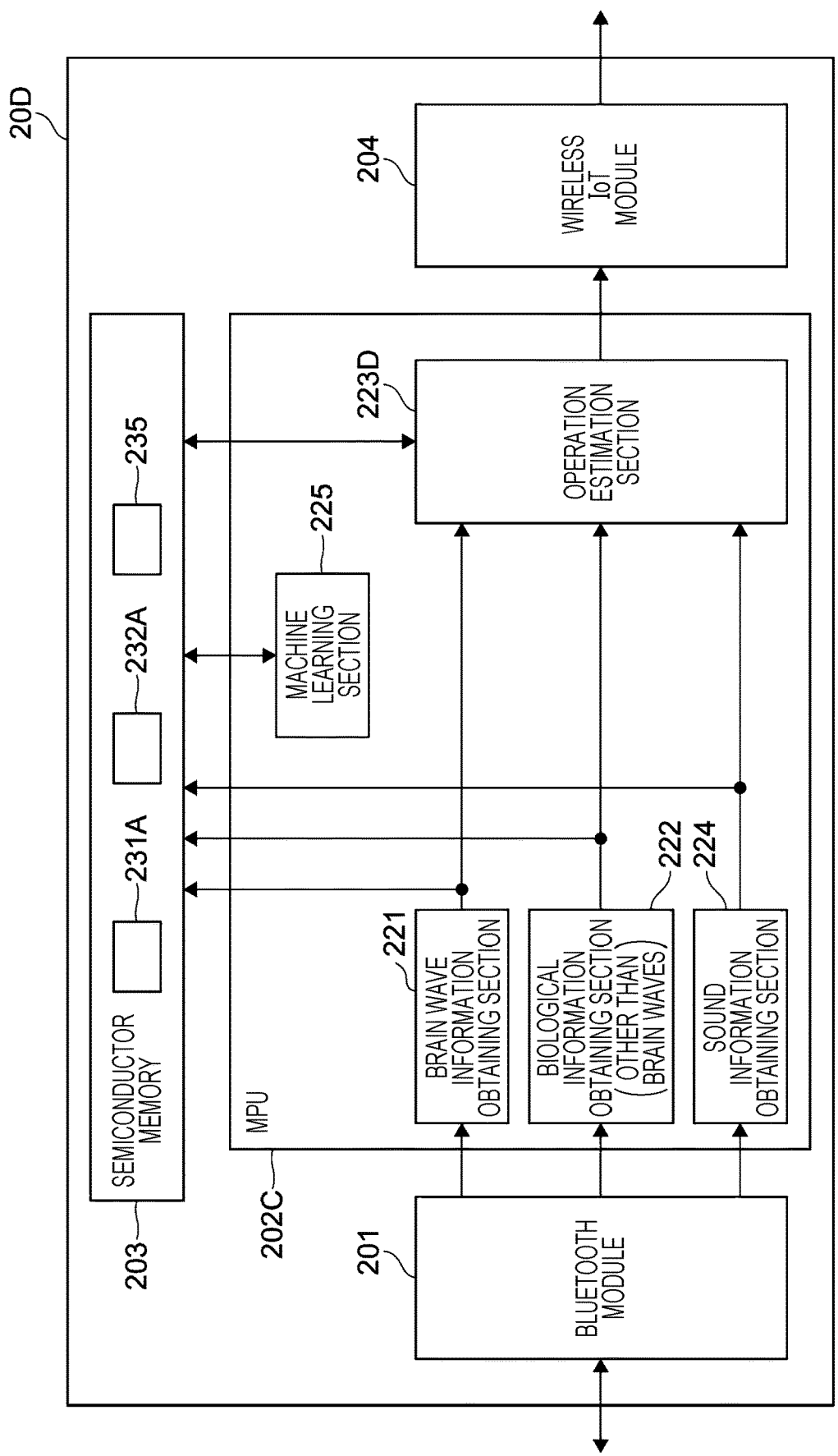
FIG. 26 is a diagram illustrating an example of the internal configuration of an information terminal used in the fifth exemplary embodiment.

FIG. 26 is a diagram illustrating an example of the internal configuration of the information terminal 20D used in the fifth exemplary embodiment. In FIG. 26, the same components as in FIG. 22 are given the same reference numerals.

The information terminal 20D illustrated in FIG. 26 is different from the information terminal 20C in that the semiconductor 203 stores a table 235. A process performed by an operation estimation section 223D is also different from that performed by the operation estimation section 223C.

FIG. 27 is a diagram illustrating an example of the table 235 storing a history of operations based on brain waves and information indicating whether the operations are correct.

The fifth exemplary embodiment is different from the fourth exemplary embodiment in that combinations of features of brain wave information and features of biological information other than brain waves are each associated with a single time point in the table 235.

The table 235 stores times at which operations based on brain waves have been performed, operations indicated by sounds uttered by the user as the user's intention, features of brain wave information, features of biological information other than brain waves, operations estimated from the features of the brain wave information, information indicating whether the operations estimated from the features of the brain wave information are correct, operations estimated from the features of the biological information other than brain waves, information indicating whether the operations estimated from the features of the biological information other than brain waves are correct, and operations indicated by operation signals transmitted to the operation target device 30.

FIG. 27 stores records at 12:45:52 and 12:46:10 on 10/15/20XX.

The operation estimation section 223D according to the present exemplary embodiment uses the table 235 to determine an operation to be transmitted to the operation target device 30.

Next, an example of a process performed by the information terminal 20D (refer to FIG. 25) by executing a program using an MPU 202D (refer to FIG. 26) will be described.

Figure 28:
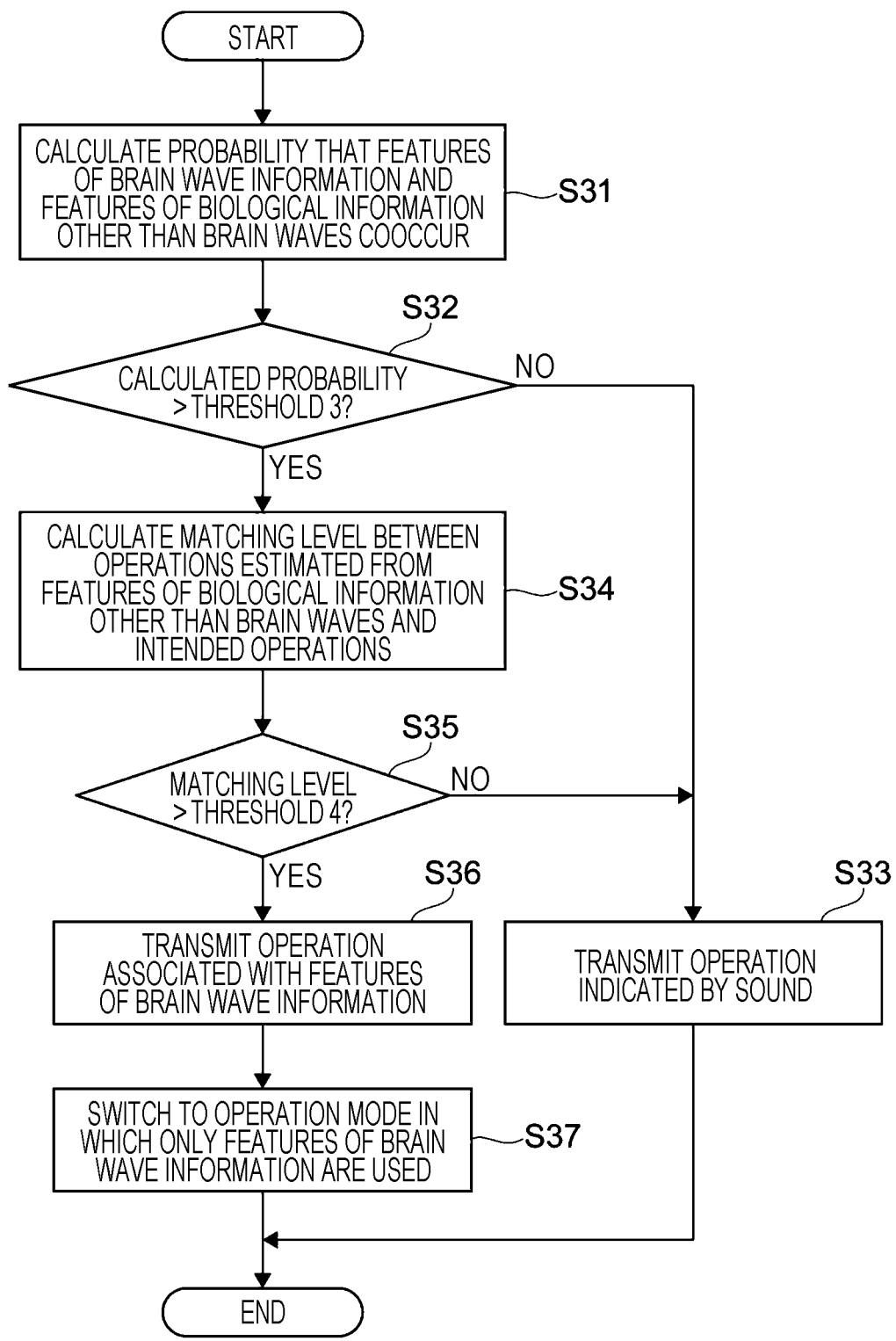
FIG. 28 is a flowchart illustrating an example of a process performed by the information terminal after the information terminal receives a digital signal including brain wave information.

FIG. 28 is a flowchart illustrating an example of a process performed by the information terminal 20D after the information terminal 20D receives a digital signal including brain wave information. "S" in FIG. 28 denotes a step.

In the present exemplary embodiment, the MPU 202D calculates a probability that features of brain wave information and features of biological information other than brain waves cooccur (S31). In the present exemplary embodiment, a probability that certain features of brain waves information occur at the same time that certain features of biological information other than brain waves occur.

The probability may be calculated while specifying on the basis of newly obtained certain features of brain wave information or all samples in the past.

The probability may be calculated using a certain period of time. This is because, even when a probability calculated from latest samples is high, for example, an operation based on brain waves might not be achieved if a large number of past samples from a period in which the user has not gotten accustomed to performing operations through brain waves are included. The probability may be calculated, therefore, while specifying a certain period of time in which samples used for the calculation have appeared.

Next, the MPU 202D determines whether the calculated probability is higher than threshold 3 (S32). Threshold 3 is, say, 95%. The percentage, however, is just an example. In addition, the user may change threshold 3. Threshold 3 is an example of a third threshold.

If a result of S32 is negative, the MPU 202D transmits an operation indicated by a sound to the operation target device 30 (S33). The result of S32 becomes negative when meaningful cooccurrence has not been detected.

If the result of S32 is positive, on the other hand, the MPU 202D calculates a matching level between operations estimated from features of biological information other than brain waves and intended operations (S34).

The result of S32 becomes positive when features of brain wave information and features of biological information other than brain waves have substantially one-to-one correspondences. In other words, a state has been established in which if the user moves certain muscles while desiring a certain operations in his/her mind, brain wave information having the same features is obtained.

Detection accuracy of the movement for swallowing saliva, for example, is high as described with reference to FIGS. 13A and 13B. When the user combines the movement of the jaw for swallowing saliva with an act of desiring an operation in his/her mind, therefore, it can be expected after the result of S32 becomes positive that an operation based only on brain waves can be quite accurately achieved.

In the present exemplary embodiment, however, an operation based on a movement of other muscles as an intentional movement of muscles is also assumed, and the following process is performed.

First, the MPU 202D calculates a matching level between operations estimated from features of biological information other than brain waves and intended operations (S34). This is because, even when there is cooccurrence between features of brain wave information and features of biological information other than brain waves, an operation based on the features of the biological information becomes incorrect if the features of the biological information other than brain waves are not ones intended by the user.

This matching level, too, may be calculated only on the basis of newly obtained features of brain wave information or all samples in the past.

The matching level may be calculated while specifying a certain period of time. This is because, even when a matching level of latest samples is high, for example, an operation based on brain waves might not be achieved if a large number of past samples from a period in which the user has not gotten accustomed to performing operations through brain waves are included. The matching level may be calculated, therefore, while limiting a period of time in which samples used for the calculation have appeared.

Next, the MPU 202D determines whether the calculated matching level is higher than threshold 4 (S35). Threshold 4 is, say, 95%. The percentage, however, is just an example. In addition, the user may change threshold 4. Threshold 4 is an example of a fourth threshold.

If a result of S35 is negative, the MPU 202D transmits an operation indicated by a sound to the operation target device 30 (S33).

If the result of S35 is positive, on the other hand, the MPU 202D transmits an operation associated with the features of the brain wave information to the operation target device 30 (refer to FIG. 25) (S36). The result of S35 becomes positive when the features of the brain wave information are likely to correctly reflect the user's intention.

In the present exemplary embodiment, the MPU 202D switches, after S36, to an operation mode in which only features of brain wave information are used (S37). As a result, operations based only on brain waves will be performed next time and later.

In the present exemplary embodiment, a state in which features that reflect the user's intention stably appear is thus identified using cooccurrence with features of biological information, whose reproducibility is higher than that of brain waves. As a result, switching from operations based on sounds to operations based on brain waves can be achieved.

Furthermore, in the present exemplary embodiment, the accuracy of correspondences between features of brain wave information and operations is improved using the machine learning section 225 (refer to FIG. 26).

The accuracy of the user's operations based on brain waves thus improves with the brain wave operation system 1D according to the present exemplary embodiment.

Other Exemplary Embodiments

Although some exemplary embodiments of the present disclosure have been described, the technical scope of the present disclosure is not limited to that of the above exemplary embodiments. It is obvious from the claims that the technical scope of the present disclosure also includes modes obtained by modifying or improving the above exemplary embodiments in various ways.

Although the movement for swallowing saliva has been taken as an example of the user's intentional movement for causing features of biological information other than brain waves in the above exemplary embodiments, the mimic muscles or the masseter muscles may be used, instead, as described above. The movement for swallowing saliva and a movement of the masseter muscles are examples of a movement of the jaw. Movements of the mimic muscles include a movement of muscles for moving the eyeballs.

In addition, although brain waves have been taken as an example of potential variations that can be measured by the earphones 10 (refer to FIG. 1), myoelectric potentials, heartbeats, heart potentials, pulsation, or pulse waves may be used, instead.

Although brain waves are measured with the earphones 10 inserted into the exterior auditory meatuses in the above exemplary embodiments, an earphone 10 may be inserted into one of the exterior auditory meatus.

Figure 29:
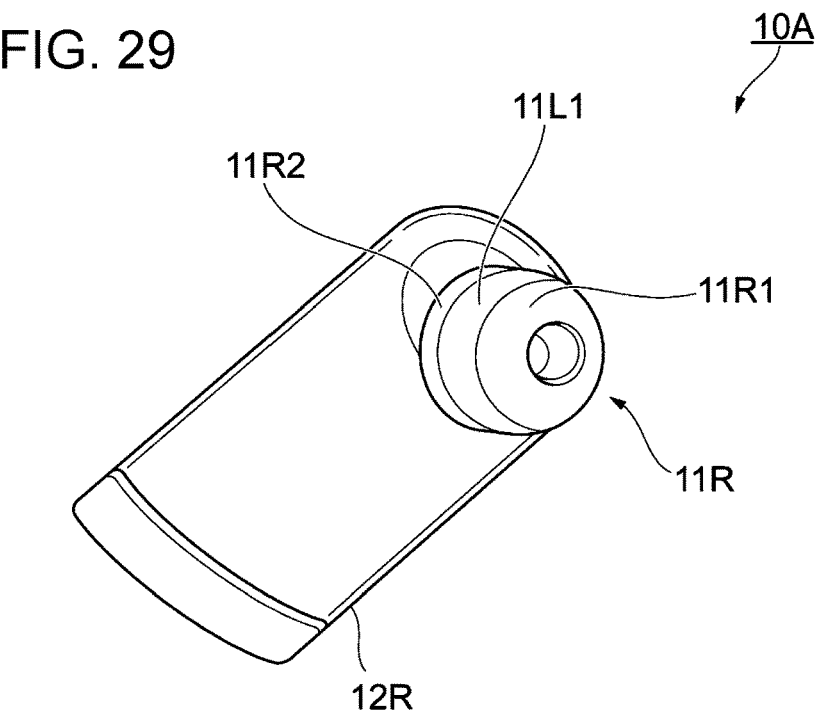
FIG. 29 is a diagram illustrating an example of the appearance of an earphone inserted into one of the ears.

FIG. 29 is a diagram illustrating an example of the appearance of an earphone 10A inserted into one of the ears. In FIG. 29, the same components as in FIG. 2 are given the same reference numerals. In the earphone 10A illustrated in FIG. 29, the earphone chip 11R is electrically separated by an insulation ring into a tip side and a body side. The electrode 11R1 is provided on the tip side, and the electrode 11L1 is provided on the body side. The electrode 11R2, which is the GND terminal, is electrically separated from the electrode 11L1 by an insulator, which is not illustrated.

With this configuration, the lithium battery 128 (refer to FIG. 3) is stored in the earphone body 12R.

Although only the mechanism for sensing potential variations is provided inside the earphones 10 (refer to FIG. 1) and the mechanism for estimating an operation from features of brain wave information or the like is provided for the information terminal 20 (refer to FIG. 1) or the like in the above exemplary embodiments, the earphones 10 may have a function of estimating an operation from features of brain wave information or the like, instead. In this case, the earphones 10 singlehandedly serve as an example of the information processing system.

In addition, although the information terminal 20 (refer to FIG. 1) or the like has a function of estimating an operation from features of brain wave information or the like in the above exemplary embodiments, a server on the Internet may execute part or the entirety of the function of estimating an operation from features of brain wave information or the like, instead. In this case, the server is an example of the information processing system.

Although the electrodes for measuring potential variations caused by brain waves and the like are provided for the earphones 10 in the above exemplary embodiments, the electrodes may be provided for another article, instead. Some specific examples will be described hereinafter.

For example, the electrodes for measuring potential variations caused by brain waves and the like may be provided for headphones that cover the auricles. In the case of headphones, the electrodes are provided at parts of earpads that come into contact with the head. At this time, the electrodes are arranged at positions where there is little hair and the electrodes can come into direct contact with the skin.

The article that comes into contact with an auricle may be a fashion accessory such as an earring or a spectacle-shaped device. These are examples of a wearable device.

Figure 30:
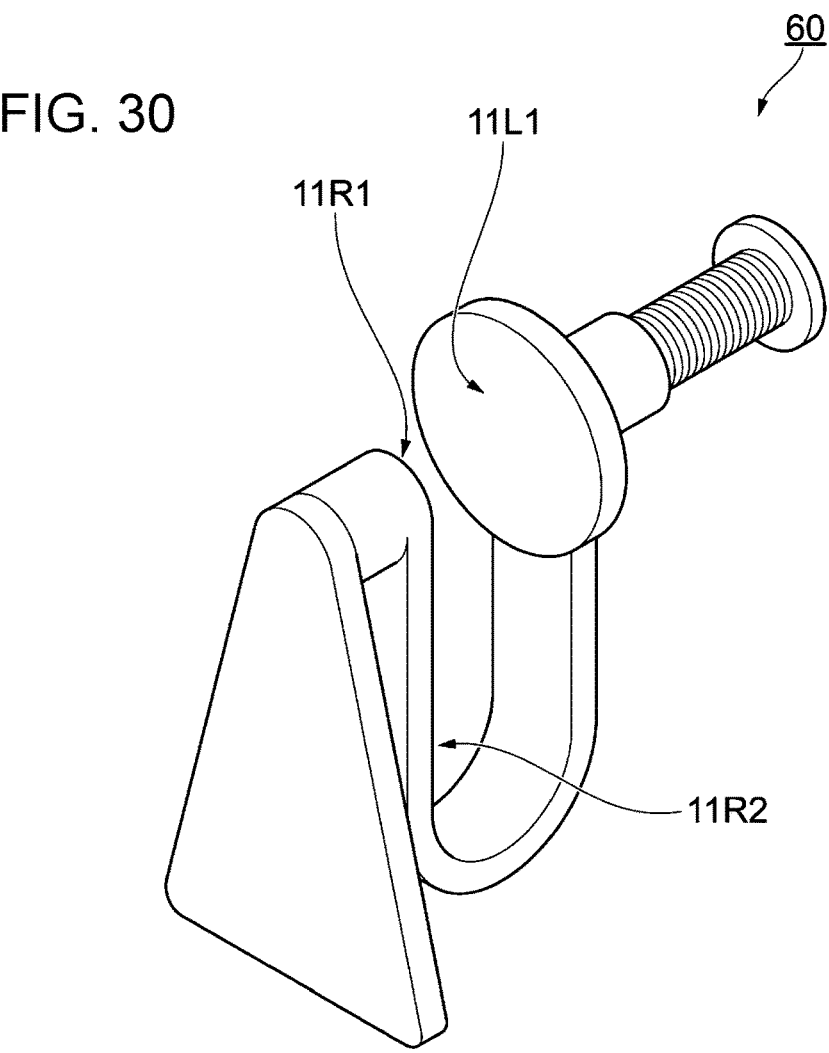
FIG. 30 is a diagram illustrating an example of an earring for which electrodes for measuring brain waves are provided.

FIG. 30 is a diagram illustrating an example of an earring 60 for which the electrodes for measuring brain waves are provided. The earring 60 illustrated in FIG. 30 includes the electrode 11R1 that comes into contact with an earlobe on a front side of the ear, the electrode 11L1 that comes into contact with the earlobe on a back side of the ear, and the electrode 11R2 that comes into contact with the earlobe at some position of a U-shaped body thereof. These electrodes are electrically separated from one another by an insulator, which is not illustrated. A battery for supplying power necessary for operation and a communication module such as Bluetooth are incorporated into an ornament, the U-shaped body, a screw for moving a plate-like member on which the electrode 11L1 is arranged, or the like.

Figure 31:
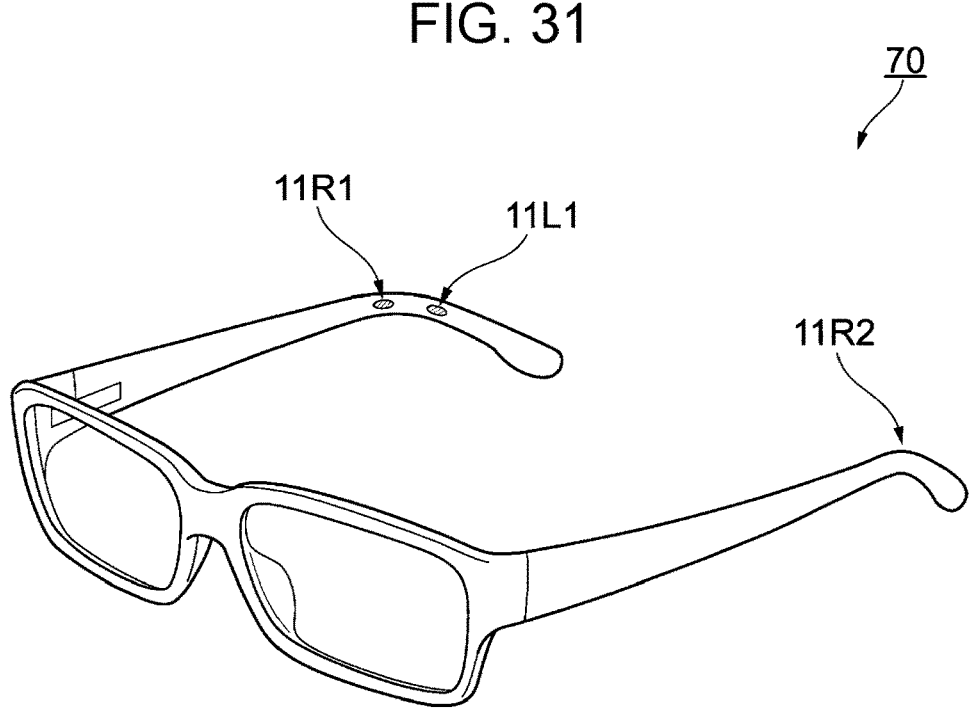
FIG. 31 is a diagram illustrating an example of spectacles for which the electrodes for measuring brain waves are provided.

FIG. 31 is a diagram illustrating an example of spectacles 70 for which the electrodes for measuring brain waves are provided. In the spectacles 70 illustrated in FIG. 31, the electrodes 11R1 and 11L1 are provided on a tip of a right temple (hereinafter referred to as a "temple tip"), and the electrode 11R2 is provided on a tip of a left temple. These electrodes are electrically separated from one another by an insulator, which is not illustrated. A battery for supplying power necessary for operation and a communication module such as Bluetooth are incorporated into a temple or a temple tip.

The electrodes for measuring brain waves may be incorporated into smart glasses or a headset called "head-mounted display" that displays information, instead. The electrodes may be mounted on a headset having a function of detecting a surrounding environment of the user and displaying an image assimilating to the surrounding environment.

Figure 32:
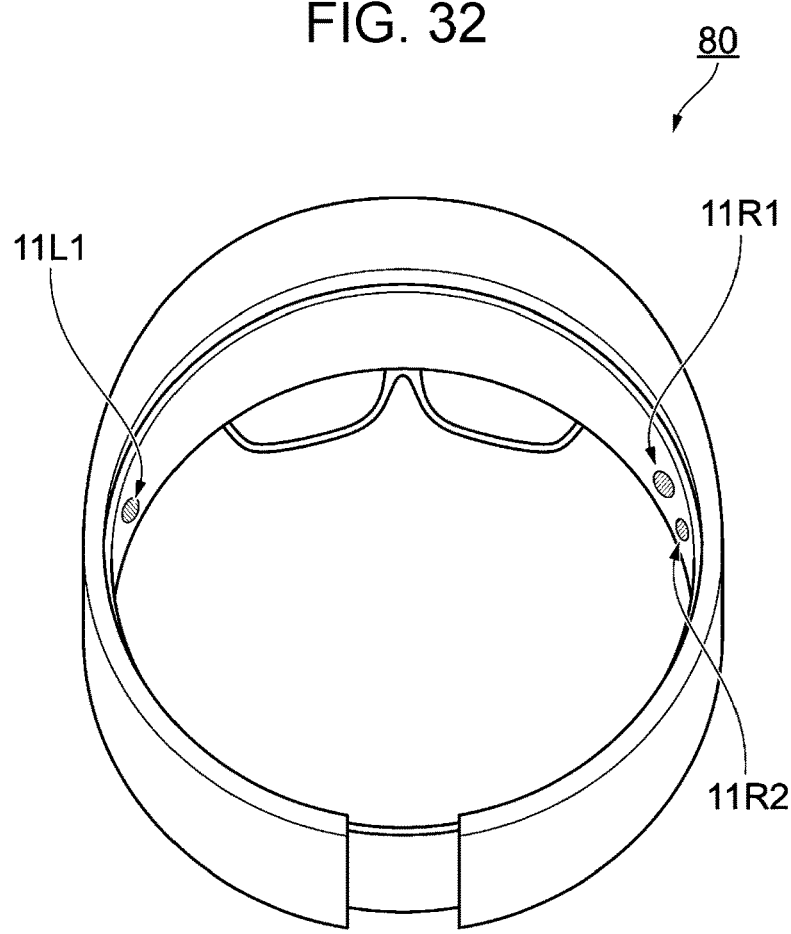
FIG. 32 is a diagram illustrating an example in which the electrodes for measuring brain waves are provided for a headset having a function of displaying an image assimilating to a surrounding environment of the user.

FIG. 32 is a diagram illustrating an example in which the electrodes for measuring brain waves are provided for a headset 80 having a function of displaying an image assimilating to the surrounding environment of the user. The headset 80 illustrated in FIG. 32 has a configuration in which the electrodes for measuring brain waves are provided for hololens (registered trademark) manufactured by Microsoft (registered trademark) Corporation. A virtual environment experienced by the user wearing the headset 80 is called "augmented reality" or "mixed reality".

In the headset 80 illustrated in FIG. 32, the electrodes 11R1, 11R2, and 11L1 are arranged in parts of a ring-shaped member that come into contact with the ears, the ring-shaped member being attached to the head. In the case of the headset 80 illustrated in FIG. 32, the electrodes 11R1 and 11R2 are arranged on a side of the right ear, and the electrode 11L1 is arranged on a side of the left ear.

A function of tracking a line of sight provided for the headset 80 may be executed to use the user's line of sight as a feature of biological information other than brain waves.

Figure 33A:
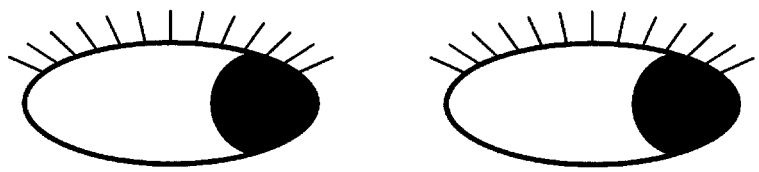
FIGS. 33A to 33D are diagrams illustrating an example in which a function of tracking a line of sight is executed to use the user's line of sight as a feature of biological information.
Figure 33B:
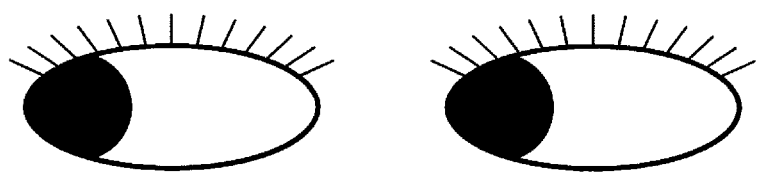
Figure 33C:
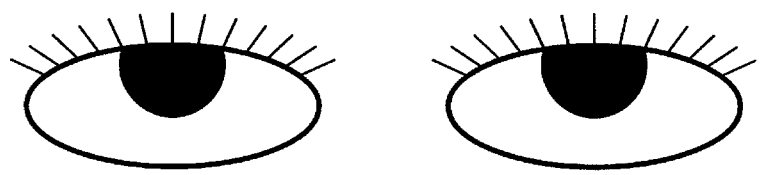
Figure 33D:
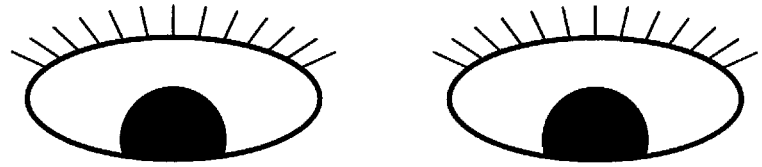

FIGS. 33A to 33D are diagrams illustrating an example in which the function of tracking a line of sight is executed to use the user's line of sight as a feature of biological information. FIG. 33A illustrates a case where the user's light of line is leftward, FIG. 33B illustrates a case where the user's line of sight is rightward, FIG. 33C illustrates a case where the user's line of sight is upward, and FIG. 33D illustrates a case where the user's line of sight is downward. Different operations are assigned to these lines of sight.

Although a case where biological information including brain waves is obtained using electrodes in contact with the user's ears in the above exemplary embodiments, a position at which the biological information including brain waves is obtained is not limited to the ears. For example, the electrodes may be provided at the forehead or another part on the head, instead.

In the case of the headset 80 (refer to FIG. 32), for example, the electrodes may be provided at some positions on the ring-shaped member attached to the head.

Although biological information including brain waves is obtained using the electrodes in contact with the user's head including the ears in the above exemplary embodiments, brain activity may be measured on the basis of changes in the amount of blood flow.

Figure 34:
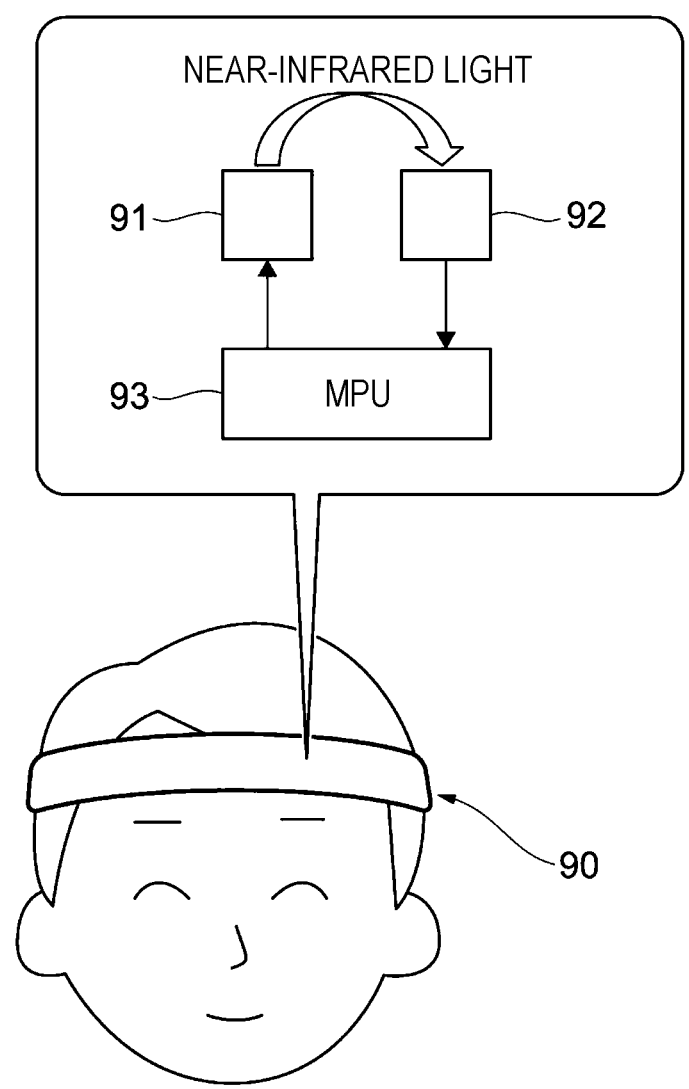
FIG. 34 is a diagram illustrating an example of a device that measures changes in the amount of blood flow caused by brain activity using near-infrared light.

FIG. 34 is a diagram illustrating an example of a headset 90 that measures changes in the amount of blood flow caused by brain activity using near-infrared light. The headset 90 includes a ring-shaped body attached to the head. Inside the body, one or plurality of probes 91 that radiate near-infrared light onto the scalp and one or plurality of detection probes 92 that receive reflected light are provided. An MPU 93 controls the radiation of near-infrared light by the probes 91 and detects features of the user's brain waves by processing signals output from the detection probes 92.

Alternatively, an MEG may be used to obtain biological information including brain waves. A tunnel magnetoresistance (TMR) sensor, for example, is used to measure magnetic fields caused by electrical activity of nerve cells of the brain.

Figure 35:
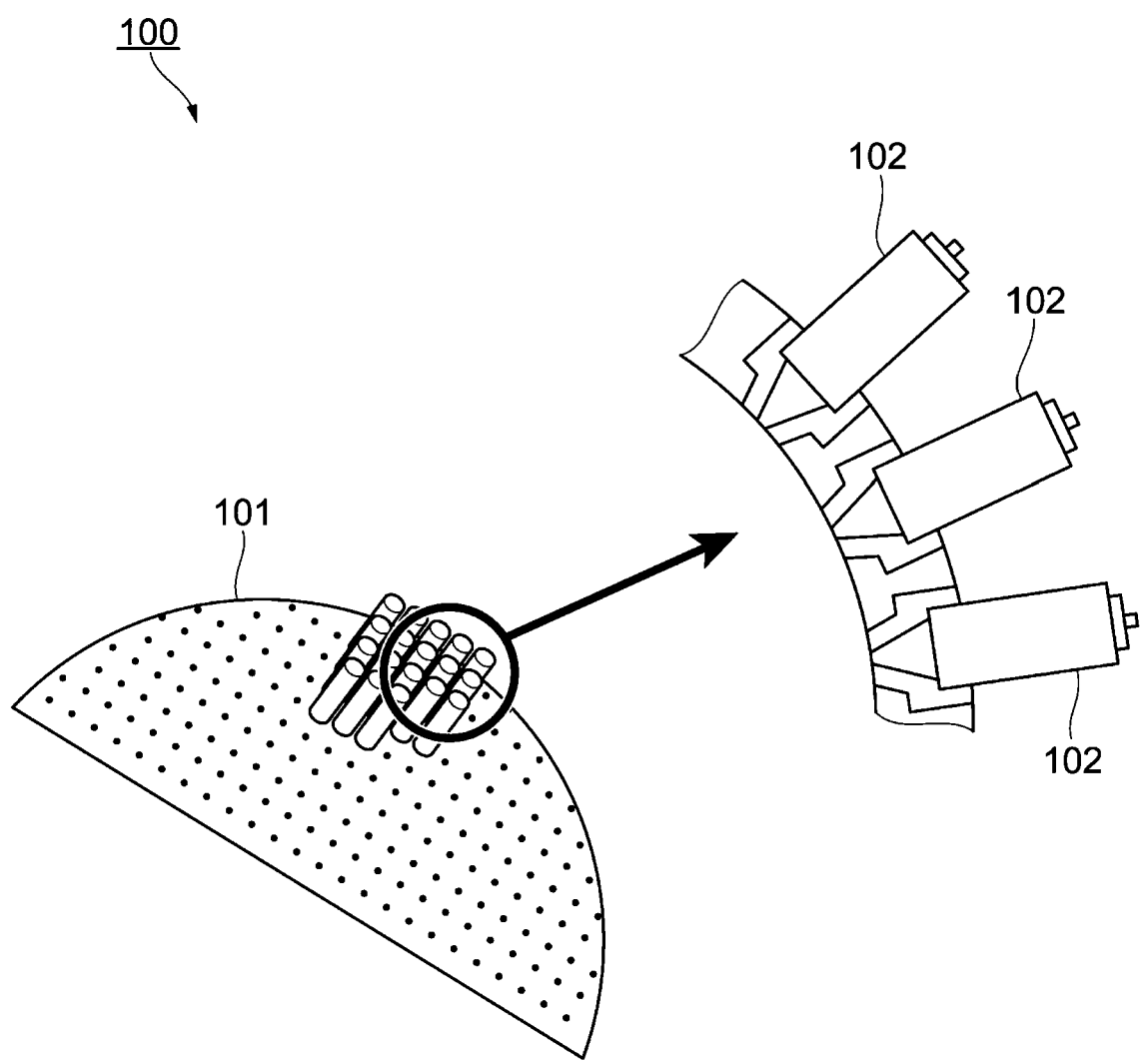
FIG. 35 is a diagram illustrating an example of a magnetoencephalography (MEG) machine.

FIG. 35 is a diagram illustrating an example of an MEG machine 100. The MEG machine 100 illustrated in FIG. 35 has a structure in which TMR sensors 102 are arranged on a cap 101 attached to the head. Outputs of the TMR sensors 102 are input to an MPU, which is not illustrated, and a magnetoencephalogram is generated. In this case, the distribution of magnetic fields in the magnetoencephalogram is used as features of the user's brain waves.

Although artifacts measured along with brain waves and a line of sight are used as biological information other than brain waves in the above exemplary embodiments, features obtained from the user's facial expressions may be used, instead. For example, a smile, a face with the eyes closed, a face with the tongue stuck out, and the like may be obtained as features.

Figure 36:
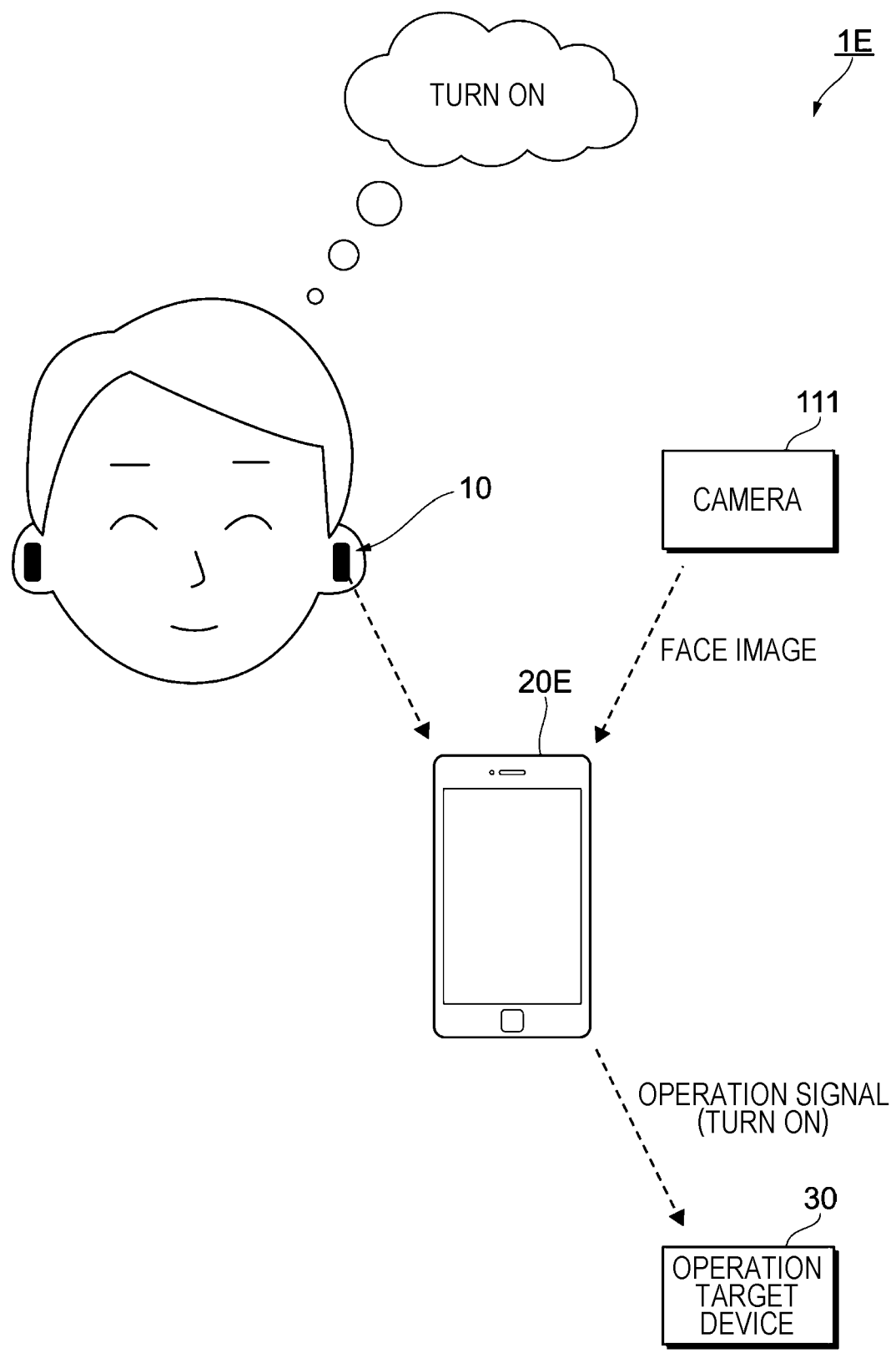
FIG. 36 is a diagram illustrating an example of a brain wave operation system that uses the user's facial expressions as features of biological information other than brain waves.

FIG. 36 is a diagram illustrating an example of a brain wave operation system 1E that uses the user's facial expressions as features of biological information other than brain waves. In FIG. 36, the same components as in FIG. 1 are given the same reference numerals.

The brain wave operation system 1E illustrated in FIG. 36 is provided with a camera 111 that captures images of the user's face. The images captured by the camera 111 are transmitted to an information terminal 20E. The information terminal 20E in this system configuration obtains features of facial expressions from the user's images using the biological information obtaining section 222 (refer to FIG. 4).

In the embodiments above, the term "MPU" refers to hardware in a broad sense. Examples of the MPU include general processors (e.g., CPU: Central Processing Unit) and dedicated processors (e.g., GPU: Graphics Processing Unit, ASIC: Application-Specific Integrated Circuit, FPGA: Field Programmable Gate Array, and programmable logic device).

In the embodiments above, the term "processor" is broad enough to encompass one processor or plural processors in collaboration which are located physically apart from each other but may work cooperatively. The order of operations of the processor is not limited to one described in the embodiments above, and may be changed.

The foregoing description of the exemplary embodiments of the present disclosure has been provided for the purposes of illustration and description. It is not intended to be exhaustive or to limit the disclosure to the precise forms disclosed. Obviously, many modifications and variations will be apparent to practitioners skilled in the art. The embodiments were chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

What is claimed is:

1. An information processing system comprising:
a processor configured to execute steps of an application program, the application program including instructions to:
measure a signal from the user, the signal comprising a first signal component that is associated with associated with a first biological information of the user and a second signal component that is associated with a second biological information different from the first biological information of the user, wherein the second signal component is an artifact in the signal;
extract first features from the first signal component;
extract second features from the second signal component;
determine user's intended operation, which is an operation intended by the user for a device to perform, based on the first features or the second features, and
transmit an operation signal to the device to perform the user's intended operation.

2. The information processing system according to claim 1, wherein the signal is measured by an electrode in contact with part of a head of the user.

3. The information processing system according to claim 2, wherein the second features derive from an intentional movement of the user.

4. The information processing system according to claim 2, wherein the part of the head is an ear.

5. The information processing system according to claim 4, wherein the second features derive from an intentional movement of the user.

6. The information processing system according to claim 1, wherein the application program includes the instructions to:
determine a first matching level between a first operation determined in accordance with the first features and user's intended operations at previous occurrences of the first features; and
in response to the first matching level being greater than a first threshold, transmit the operation signal to the device to perform the first operation determined in accordance with the first features.

7. The information processing system according to claim 1, wherein the application program includes instructions to:
determine a first matching level between a first operation determined in accordance with the first features and user's intended operations at previous occurrences of the first features;
in response to the first matching level being lower than the first threshold, determine a second matching level between a second operation determined in accordance with the second features and user's intended operations at previous occurrences of the second features; and
in response to the second matching level being greater than a second threshold, transmit a second operation signal to the device to perform the second operation.

8. The information processing system according to claim 1, wherein the application program includes instructions to determine the user's intended operation by using a model that is obtained based on data of the first biological information, the second biological information, and user's intended operations.

9. The information processing system according to claim 8, wherein the model varies according to the user.

10. The information processing system according to claim 8, wherein the user's intended operations are recognized from speech.

11. The information processing system according to claim 1, wherein the application program includes instructions to:
   determine a first matching level between a first operation determined in accordance with the first features and user's intended operations at previous occurrences of the first features;
   in response to the first matching level being lower than a first threshold, determining a second matching level between a second operation determined in accordance with the second features and user's intended operations at previous occurrences of the second features; and
   in response to the second matching level being lower than a second threshold, transmit a third operation signal to the device to perform a third operation specified by speech produced by the user.

12. The information processing system according to claim 1, wherein the second features derive from an intentional movement of the user.

13. The information processing system according to claim 1, wherein the application program includes instructions to, in response to a matching level between a first operation determined in accordance with the first features and user's intended operations at previous occurrences of the first features being larger than a first threshold, transmit an operation signal to the device to perform the first operation determined in accordance with the first features.

14. The information processing system according to claim 1, wherein the application program includes instructions to:
   determine a probability that the first features and the second features cooccur,
   in response to the probability being larger than a third threshold, determine a second matching level between a second operation determined in accordance with the second features and user's intended operations at previous occurrences of the second features; and
   in response to the second matching level being larger than a fourth threshold, transmit a first operation signal to the device to perform a first operation determined in accordance with the first features.

15. The information processing system according to claim 1, wherein the first biological information is obtained by a sensor that is not in contact with the user.

16. The information processing system according to claim 15,
   wherein the second biological information is a facial expression of the user.

17. The information processing system according to claim 15, wherein the second biological information is a sight line of the user.

18. The information processing system according to claim 1, wherein the information processing system is a wearable device.

19. The information processing system according to claim 1, wherein the information processing system is a computer communicably connected to a wearable device.

20. The information processing system according to claim 1, the first biological information being brain waves of the user and the second biological information being biological information that is different from the brain waves of the user.

21. The information processing system according to claim 1, wherein both the first biological information and the second biological information are associated with the user's intended operation.

22. The information processing system according to claim 1, wherein the information processing system is a wearable device that is wearable on user's ears.

23. A non-transitory computer readable medium, wherein the non-transitory computer readable medium stores an application program including instructions for a computer to execute a process comprising:
   measuring a signal from a user, the signal comprising a first signal component that is associated with a first signal component of the user associated with a first biological information of the user and a second signal component that is associated with a second biological information different from the first biological information of the user, wherein the second signal component is an artifact in the signal;
   extracting a first feature from the first signal component;
   extracting a second feature from the second signal component;
   determine user's intended operation, which is an operation intended by the user for a device to perform, based on the first feature or the second feature, and
   transmit an operation signal to the device to perform the user's intended operation.

24. An information processing system comprising:
a processor configured to execute steps of an application program, the application program including instructions to determine user's intended operation, which is an operation intended by the user for a device to perform, based on first features or second features extracted from a signal measured from the user, the instructions comprising:
   determining a first matching level between a first operation determined in accordance with the first features and user's intended operations at previous occurrences of the first features;
   if the first matching level is greater than a first threshold, transmitting a first operation signal to the device to perform the user's intended operation;
   if the first matching level is lower than the first threshold, determining a second matching level between a second operation determined in accordance with the second features and user's intended operations at previous occurrences of the second features; and in response to the second matching level being greater than a second threshold, transmitting a second operation signal to the device to perform the user's intended operation.

* * * * *